US009463190B2

(12) United States Patent
Zesiewicz et al.

(10) Patent No.: US 9,463,190 B2
(45) Date of Patent: Oct. 11, 2016

(54) METHODS OF TREATING DISEASE-INDUCED ATAXIA AND NON-ATAXIC IMBALANCE

(75) Inventors: Theresa A. Zesiewicz, Tampa, FL (US); Kelly L. Sullivan, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 724 days.

(21) Appl. No.: 12/934,913

(22) PCT Filed: Mar. 31, 2009

(86) PCT No.: PCT/US2009/038948
§ 371 (c)(1),
(2), (4) Date: Oct. 28, 2010

(87) PCT Pub. No.: WO2009/146031
PCT Pub. Date: Dec. 3, 2009

(65) Prior Publication Data
US 2011/0059905 A1 Mar. 10, 2011

Related U.S. Application Data

(60) Provisional application No. 61/076,343, filed on Jun. 27, 2008, provisional application No. 61/056,173, filed on May 27, 2008, provisional application No. 61/043,522, filed on Apr. 9, 2008, provisional application No. 61/041,408, filed on Apr. 1, 2008, provisional application No. 61/041,069, filed on Mar. 31, 2008.

(51) Int. Cl.
*A61K 31/4985* (2006.01)
*A61K 31/138* (2006.01)
*A61K 31/44* (2006.01)
*A61K 31/445* (2006.01)
*A61K 31/498* (2006.01)
*A61K 31/55* (2006.01)
*A61K 45/06* (2006.01)

(52) U.S. Cl.
CPC ......... *A61K 31/4985* (2013.01); *A61K 31/138* (2013.01); *A61K 31/44* (2013.01); *A61K 31/445* (2013.01); *A61K 31/498* (2013.01); *A61K 31/55* (2013.01); *A61K 45/06* (2013.01)

(58) Field of Classification Search
CPC ..................... A61K 31/4985; A61K 31/445
See application file for complete search history.

(56) References Cited

U.S. PATENT DOCUMENTS

| | | | |
|---|---|---|---|
| 5,316,011 A | 5/1994 | Weinstein et al. | |
| 5,381,806 A | 1/1995 | Weinstein et al. | |
| 5,602,257 A | 2/1997 | Zoltewicz et al. | |
| 5,741,802 A | 4/1998 | Kem et al. | |
| 5,914,328 A | 6/1999 | Lin et al. | |
| 5,948,793 A | 9/1999 | Abreo et al. | |
| 5,977,144 A | 11/1999 | Meyer et al. | |
| 6,034,079 A | 3/2000 | Sanberg et al. | |
| 6,196,976 B1 | 3/2001 | Christy | |
| 6,303,638 B1 | 10/2001 | Latli et al. | |
| 6,410,550 B1 | 6/2002 | Coe et al. | |
| 6,538,003 B1 | 3/2003 | Galli et al. | |
| 6,605,610 B1 | 8/2003 | Coe et al. | |
| 6,630,491 B1 | 10/2003 | Zoltewicz et al. | |
| 6,809,105 B2 | 10/2004 | Schrimpf et al. | |
| 6,833,370 B1 | 12/2004 | Schrimpf et al. | |
| 6,846,817 B2 | 1/2005 | Efange | |
| 6,890,927 B2 | 5/2005 | Bogle et al. | |
| 6,979,695 B2 | 12/2005 | Caldwell et al. | |
| 7,045,538 B2 | 5/2006 | Caldwell et al. | |
| 7,244,745 B2 * | 7/2007 | Herbert et al. | 514/333 |
| 7,265,119 B2 | 9/2007 | Bogle et al. | |
| 7,429,664 B2 | 9/2008 | Xie et al. | |
| 7,718,677 B2 | 5/2010 | Quik et al. | |
| 2002/0028809 A1 | 3/2002 | Imoto et al. | |
| 2002/0052497 A1 | 5/2002 | Caldwell et al. | |
| 2004/0192594 A1 | 9/2004 | Reid et al. | |
| 2004/0204862 A1 | 10/2004 | Wainer et al. | |
| 2004/0235850 A1 | 11/2004 | Waterman | |
| 2006/0084656 A1 | 4/2006 | Ziegler et al. | |
| 2006/0211686 A1 | 9/2006 | Kohlhaas et al. | |
| 2007/0224690 A1 | 9/2007 | Busch et al. | |
| 2009/0012127 A1 | 1/2009 | Simpson et al. | |

FOREIGN PATENT DOCUMENTS

| | | |
|---|---|---|
| WO | 92/15306 | 9/1992 |
| WO | 96/40682 | 12/1996 |
| WO | 99/10338 | 3/1999 |
| WO | 99/32480 | 7/1999 |
| WO | 99/65876 | 12/1999 |
| WO | 00/71534 A1 | 11/2000 |
| WO | 00/75710 A2 | 12/2000 |
| WO | 01/62736 A1 | 8/2001 |

(Continued)

OTHER PUBLICATIONS

Spinocerebellar ataxia. http://wikipedia.org/wiki/Spinocerebellar ataxia (Mar. 18, 2014).*
Al-Rejaie, S., et al., Behavioral Interaction Between Nicotine and Ethanol: Possible Modulation by Mouse Cerebellar Glutamate, Alcoholism: Clinical and Experimental Research, 2006, 30(7), 1223-1233.
Arneric, S.P., et al., Neuronal nicotinic receptors: A perspective on two decades of drug discovery research, Biochemical Pharmacology, 2007, 74, 1092-1101.

(Continued)

*Primary Examiner* — Robert C Hayes
(74) *Attorney, Agent, or Firm* — Saliwanchik, Lloyd & Eisenschenk

(57) ABSTRACT

Methods for treatment of disease-induced ataxia and non-ataxic imbalance are disclosed. The methods involve treating a patient with a compound having nicotinic acetylcholine receptor activity.

4 Claims, 2 Drawing Sheets

(56) References Cited

FOREIGN PATENT DOCUMENTS

| WO | 01/81326 A1 | 11/2001 |
|---|---|---|
| WO | 2006/133303 A1 | 12/2006 |
| WO | 2009/143019 A2 | 11/2009 |

OTHER PUBLICATIONS

Assadi, M., et al., Treatment of spinocerebellar ataxia with buspirone, Journal of the Neurological Sciences, 2007, 260, 143-146.
Beck, A.T., et al., An inventory for measuring depression, Archives of General Psychiatry, 4, 561-571.
Campuzano, V., et al., Friedreich's Ataxia: Autosomal Recessive Disease Caused by an Intronic GAA Triplet Repeat Expansion, Science, 1996, 271(5254), 1423-1427.
Chen, W.A., et al., Nicotine Decreases Blood Alcohol Concentration in Neonatal Rats, Alcoholism: Clinical and Experimental Research, 2001, 25, 1072-1077.
Chen, W.A., et al., Long-term nicotine exposure reduces Purkinje cell number in the adult rat cerebellar vermis, Neurotoxicology and Teratology, 2003, 25(3), 329-334.
Cossee, M. et al., Evolution of the Friedreich's ataxia trinucleotide repeat expansion: Founder effect and premutations, Proceedings of the National Academy of Sciences, 1997, 94, 7452-7457.
Cossee, M., et al., Friedreich's Ataxia: Point Mutations and Clinical Presentation of Compound Heterozygotes, American Neurological Association, 1999, 45(2), 200-206.
De Smet, Y, et al., Effect of Gamma-Vinyl GABA in Friedreich's Ataxia, Canadian Journal of Neurological Sciences, 1982, 9(2), 171-173.
Dube, G. R., et al., Loss of functional neuronal nicotinic receptors in dorsal root ganglion neurons in a rat model of neuropathic pain, Neuroscience Letters, 2005, 376, 29-34.
Falk, L., et al., Smoking during early pregnancy affects the expression pattern of both nicotinic and muscarinic acetylcholine receptors in human first trimester brainstem and cerebellum, Neuroscience, 2005, 132, 389-397.
Frykberg, R. G., et al., Diabetic Food Disorders: A clincial practice guideline (2006 revision), Supplemental to The Journal of Foot and Ankle Surgery, 2006, 45(5), S2-S66.
Inoue, K., et al., Friedreich's Ataxia selectively involves the large neurons of the Dorsal Root Ganglia, Transactions of the American Neurological Association, 1979, 104, 75-76.
Jacquemont, S., et al., Fragile X Premutation Tremor/Ataxia Syndrome: Molecular, Clinical, and Neuroimaging Correlates, American Journal of Human Genetics, 2003, 72(4), 869-878.
Kark, R. A. P., et al., Double-blind, triple-crossover trial of low doses of oral physostigmine in inherited ataxias, Neurology, 1981, 31(3), 288-292.
Katz, et al., A study of the desensitization produced by acetylcholine at the motor end-plate, Journal of Physiology, 1967, 138, 63-80.
Kem, W. R., Structure and Action of Nemertine Toxins, American Zoologist, 1985, 25(1), 99-111.
Kem, W. R., A study of the occurrence of anabaseine in Paranemertes and other Nemertines, Toxicon, 1971, 9, 23-32.
Kleissen, R. F. M., et al., Electromyography in the biomechanical analysis of human movement and its clinical application, Gait & Posture, 1998, 8(2), 143-158.
Leone, M., et al., Ataxia clinical rating scale in Friedreich disease, Italian Journal of Neurological Sciences, 1986, 7 (1), 61-62.
Lynch, D. R., et al., Measuring Friedreich ataxia Complementary features of examination and performance measures, Neurology, 2006, 66, 1711-1716.
Macor, J. E., et al., The 5-HT3 Antagonist Tropisetron (ICS 205-930) is a Potent and Selective α7 Nicotinic Receptor Partial Agonist, Bioorganic & Medicinal Chemistry Letters, 2001, 11, 319-321.
Mihalak, K. B., et al, Varenicline Is a Partial Agonist at α4β2 and a Full Agonist at α7 Neuronal Nicotinic Receptors, Molecular Pharmacology, 2006, 70(3), 801-805.
Pereira, C. B., et al., Smoking and balance: correlation of nicotine-induced nystagmus and postural body sway, NeuroReport, 2001, 8, 1223-1226.
Peterson, P. L, et al., The treatment of Friedreich's ataxia with amantadine hydrochloride, Neurology, 1988, 38(9), 1478-1480.
Reaz, M. B. I., et al., Techniques of EMG signal analysis: detection, processing, classification and applications, Biological Procedures Online, 2006,8(1), 11-35.
Rueter, L. E., et al., Peripheral and central sites of action for A-85380 in the spinal nerve ligation model of neuropathic pain, Pain, 2003, 103(3), 269-276.
Schmitz-Hubsch, T., et al., Scale for the assessment and rating of ataxia Development of a new clinical scale, Neurology, 2006, 66, 1717-1720.
Smith, A. D., et al., Mouse cerebellar nicotinic-cholinergic receptor modulation of Δ9-THC ataxia: Role of the α4β2 subtype, Brain Research, 2006, 1115(1), 16-25.
Spillane, J. D., The effect of nicotine on spinocerebellar ataxia, British Medical Journal, 1955, 1345-1351.
Subramony, S. H., et al., Measuring Friedreich ataxia: Interrater reliability of a neurologic rating scale, Neurology, 2005, 64(7), 1261-1262.
Trouillas, P. et al., International cooperative ataxia rating scale for pharmacological assessment of the cerebella syndrome, Journal of the Neurological Sciences, 1997, 145(2), 205-211.
Trouillas, P., et al., Levorotatory form of 5-Hydrotrytophan in Friedreich's Ataxia, Archives of Neurology, 1995, 52 (5), 456-460.
West, R., et al., Effect of varenicline and bupropion SR on craving, nicotine withdrawal symptoms, and rewarding effects of smoking during a quit attempt, Psychopharmacology, 2008, 197(3), 371-377.
PCT Search Report for PCT/US2009/038948, dated Oct. 29, 2009.
Klockgether, T., Update on degenerative ataxis, Current Opinion in Neurology, 2011, 24, 339-345.
Desanty, K.P., et al., Cannabinoid-induced motor incoordination through there cerebellar CB1 receptor in mice, Pharmacology, Biochemistry and Behavior, 2001, 69, 251-259.
Patel, S. et al., Cannabinoid CB1 receptor agonists product cerebellar dysfunction in mice, The Journal of Pharmacology and Experimental Therapies, 2001, 297, 629-237.
Zesiewicz, T. et al., A randomized trial of varenicline (Chantix) for the treatment of spinocerebellar ataxia type 3, Neurology, 2012, 78, 545-558.
Zesiewicz, T. et al., Treatment of imbalance with varenicline Chantix ⁿ : report of a patient with a fragile X tremor/ataxia syndrome, Acta Neurologica Scandinavica, Feb. 2009, 119(2), 135-138.
Zesiewicz, T., et al., Treatment of ataxia and imbalance with varenicline (Chantix): report of 2 patients with spinocerebellar axtaxia (types 3 and 14), Clinical Neuropharmacology, Nov.-Dec. 2008, 31(6), 363-365.
Zesiewicz, T., et al., Subjective Improvement in Proprioception in 2 Patients With Atypical Friedreich Ataxia Treated With Varenicline (Chantix), Clinical Neuromuscular Disease, Jun. 2009, 10(4), 191-193.
Megna et al., Ataxia From Lithium Toxicity Successfully Treated With High-Dose Buspirone: A Single-Case Experimental Design, 2001, Arch Phys Med Rehabil, 82, 1145-1148.
Wecker, L. et al., Neuronal nicotinic receptor agonists improve gait and balance in olivocerebellar ataxia, 2013, Neuropharmacology, 73, 75-86.
Presori, F. et al., Gating of Long-Term Potentiation by Nicotinic Acetylcholine Receptors at the Cerebellum Input Stage, 2013, PLoS One, 8(5), e64828, 11 pages.
United States Patent and Trademark Office, Office Action issued on U.S. Appl. No. 12/993,457 on Mar. 5, 2013, 9 pages.
Graham, A. et al. "Immunohistochemical localisation of nicotinic acetylcholine receptor subunits in human cerebellum" *Neuroscience*, 2002, 113(3):493-507.
PCT Search Report for PCT/US2009/044155, dated Jan. 25, 2010.
Smith, A.D. et al. "Involvement of the $\alpha_4\beta_2$ nicotinic receptor subtype in nicotine-induced attenuation of $\Delta^9$-THC cerebellar ataxia: Role of cerebellar nitric oxide" *Pharmacology Biochemistry and Behavior*, 2007, 86:103-112.

\* cited by examiner

FIGURE 1

| Start | Week 1 | Week 7 | Week 8, day 3 | Week 10 | Week 11 |
|---|---|---|---|---|---|
| Patient started varenicline. | Patient noted improved walking and balance. | First clinic evaluation. Varenicline stopped after this visit. | Patient noted worsening of ataxia and imbalance off varenicline. | Patient returned to clinic off varenicline. | Patient resumed varenicline. |

METHODS OF TREATING DISEASE-INDUCED ATAXIA AND NON-ATAXIC IMBALANCE

CROSS-REFERENCE TO RELATED APPLICATIONS

The present application claims the benefit of U.S. Provisional Application Ser. No. 61/041,069, filed on Mar. 31, 2008; Ser. No. 61/041,408, filed on Apr. 1, 2008; Ser. No. 61/043,522, filed on Apr. 9, 2008; Ser. No. 61/056,173, filed on May 27, 2008; and Ser. No. 61/076,343, filed on Jun. 27, 2008, each of which is hereby incorporated by reference herein in its entirety.

BACKGROUND

The present disclosure generally relates to methods for treatment of disease-induced ataxia and non-ataxic imbalance. These symptoms can be treated in a patient by administering to the patient a compound having nicotinic acetylcholine receptor activity.

The role of nicotine on the human cerebellum is unclear. Nicotinic receptors appear responsible for disorders like Alzheimer's disease, anxiety, drug addition, epilepsy, Parkinson's Disease, schizophrenia, and Tourette's Syndrome. A report by Pereira et al. (NeuroReport 2001, 8, 1223-1226) showed that nicotine was associated with postural imbalance in non-smokers and occasionally in smokers, and also contributed to nystagmus and body sway (Spillane J D, Br. Med. J. 1955, 2: 1345, 1345-1351). Prenatal or neonatal nicotine exposure is thought to interfere with brain development in both human and animal studies. In fact, nicotine crosses the placenta (Al-Rejaie et al., Alcohol Clin. Exp. Res. 2006, 30(7), 1223-33). Smoking during pregnancy has been associated with miscarriage, sudden infant death syndrome (SIDS), and neurobehavioral disturbances including hyperactivity, depression, and anxiety (Smith et al., Brain Res. 2006, 1115(1), 16-25; Katz et al., J. Physiol. 1967, 138, 63-80). One study found that concurrent exposure of the human brain to alcohol and nicotine during a brain growth spurts reduced the total number of Purkinje cells (Arneric et al., Biochemical Pharmacology 2007, 74, 1092-1101). Another study compared the expression of nicotinic and muscarinic acetylcholine receptors in the first trimester in the pons, medulla oblongata, and cerebellum in 5-12 week gestation abortus of smoking and non-smoking women (Katz et al., J. Physiol. 1967, supra). The gene expression pattern of both α4 and α7 nicotinic receptor subunits in these regions was altered after smoking. These findings suggest that early prenatal nicotine exposure affects the normal developmental pattern of the human fetal cholinergic system.

Unlike nicotine, selective activation of nicotinic acetylcholine receptors, such as the α4β2 nicotinic acetylcholine receptor, may improve ataxia (Al-Rejaie et al., Alcohol Clin. Exp. Res. 2006, supra). Partial agonism of this receptor has been shown to decrease ataxia in animal models that was induced by alcohol (Al-Rejaie et al., Alcohol Clin. Exp. Res. 2006, supra) or tetrahydrocannabinoid (Smith et al., Brain Res. 2006, supra). Nicotinic acetylcholine receptors are rapidly desensitized by up-regulation (Katz et al., J. Physiol. 1967, supra), and partial $\alpha_4\beta_2$ nicotinic acetylcholine receptors agonists like varenicline may paradoxically behave as antagonists rather than agonists (Arneric et al., Biochemical Pharmacology 2007, supra).

The $\alpha_4\beta_2$ receptor in the mammalian brain has been linked to reward, tolerance and sensitization of nicotine (West et al., Psychopharmacology 2008; 197(3):371-7). In vivo studies of nicotinic acetylcholine receptors found an increased binding of [3H]nicotine in several areas of the brain in smokers, with prominent regional differences of distribution volumes in the cerebellum and brain stem, with an increased uptake in smokers compared to non-smokers (West et al., Psychopharmacology 2008, supra).

Varenicline is a recently-developed drug structurally based on cytisine, used as a prescription drug to combat smoking addition. Varenicline is a nicotinic receptor agonist, acting as a partial agonist of many nicotinic acetylcholine receptors, including the $\alpha_4\beta_2$ subtype, found in the cerebellum (Schmitz-Hübsch et al., Neurology 2006, supra). Recent reports also show varenicline acts as a potent, full agonist of the $\alpha_7$ receptor subtype (K. Minalak, et al., Molec. Pharm., 70(3):801-805 (2006)). As noted above, nicotinic acetylcholine receptors rapidly desensitize by up-regulation of the active agent leading to the hypothesis that certain agents may act on these receptors functionally as antagonists, rather than as agonists.

Multiple neurodegenerative diseases and toxic exposures can lead to the progressive loss of the ability to coordinate movements. Symptoms of these physically devastating diseases and conditions include ataxia, imbalance, and sensory abnormalities. Ataxia and imbalance caused by, among other things, cerebellar disease, progressive supranuclear palsy (PSP) and atypical parkinonsims, currently have no treatment or cure.

SUMMARY OF THE DISCLOSURE

Among the various aspects of the present invention is the provision of methods for treatment of disease-induced ataxia and non-ataxic imbalance.

Briefly, therefore, the present invention is directed in one aspect to a method of treating disease-induced ataxia or non-ataxic imbalance in a human, the method comprising administering to the human a compound having nicotinic acetylcholine receptor activity.

Another aspect of the invention is directed to a method of treating disease-induced ataxia or non-ataxic imbalance in a human, the method comprising: determining a baseline measurement of ataxia or non-ataxic imbalance in the human and thereafter administering to the human a compound having nicotinic acetylcholine receptor activity; and determining a second measurement of ataxia or non-ataxic imbalance in the human during or after administration of the compound, wherein an improvement in the second measurement relative to the baseline measurement indicates treatment of the ataxia or non-ataxic imbalance.

Another aspect of the invention is directed to a method of treating disease-induced ataxia or non-ataxic imbalance in a human, the method comprising: determining a baseline measurement of ataxia or non-ataxic imbalance in the human and thereafter administering to the human a compound having nicotinic acetylcholine receptor activity; and determining a second measurement of ataxia or non-ataxic imbalance in the human at least one month after administration of the compound has ceased; wherein the second measurement is improved relative to the baseline measurement.

Another aspect of the invention is directed to a method of treating disease-induced ataxia or non-ataxic imbalance in a human, the method comprising administering to the human a compound having nicotinic acetylcholine receptor activity, wherein a second measurement of ataxia or non-ataxic imbalance measured after ceasing administration of the compound is improved relative to a baseline measurement of ataxia or non-ataxic imbalance measured prior to administration of the compound.

Another aspect of the invention is directed to use of a compound having nicotinic acetylcholine receptor activity in the manufacture of a medicament for the treatment of disease-induced ataxia or non-ataxic imbalance.

Another aspect of the invention is directed to an (i) aryl-fused azapolycyclic compound; (ii) pyridopyranoazepine; (iii) aryl-substituted olefinic amine compound; (iv) benzylidene- or cinnamylidene-anabaseine compound; (v) heterocyclic ether compound; (vi) 3-pyridyloxyalkyl heterocyclic ether compound; (vii) N-substituted diazabicyclic compound; (viii) heterocyclic substituted amino azacycle compound; or (ix) indazole, benzothioazole, or benzoisothiazole compound for use in the therapeutic treatment of disease-induced ataxia or non-ataxic imbalance.

Another aspect of the invention is directed to an aryl-fused azapolycyclic compound for use in the therapeutic treatment of disease-induced ataxia or non-ataxic imbalance.

In each of these and other aspects, in one general embodiment the compound may selected from the group consisting of ABT-089, ABT-894, alpha-bungarotoxin, anabaseine, bupropion, buspirone, BW284c51, cytisine, dianicline (SSR591813), dihydro-beta-erythoidine, DMXB, DMXB-A (GTS-21), diazoxon, donepezil, exelon, fluoxetine, galantamine, huperzine A, ispronicline (TC-1734/AZD-3480), lobeline, mecamylamine, MEM3454, MEM63908, methyllycaconitine, nefazodone, octanol/ethanol, OmIA, paroxetine, sertraline, tacrine, TC-2559, TC-5214 ((S)-(+)-mecamylamine), TC-5619, tebanicline (ABT-594), varenicline, venlafaxine, XY4083, and combinations thereof. In one general embodiment, the compound is selected from the group consisting of ABT-089, ABT-894, bupropion, cytisine, dianicline (SSR591813), DMXB-A (GTS-21), ispronicline (TC-1734/AZD-3480), lobeline, mecamylamine, methyllycaconitine, TC-2559, TC-5214 ((S)-(+)-mecamylamine), tebanicline (ABT-594), varenicline, and combinations thereof. In another general embodiment, the compound is selected from the group consisting of donepezil, exelon, fluoxetine, galantamine, huperzine A, MEM3454, MEM63908, tacrine, XY4083, and combinations thereof. In another general embodiment of these and other aspects, the compound is, for example, a smoking cessation agent that operates through nicotinic acetylcholine receptor activity; in one particular embodiment, for example, the compound is varenicline.

Other objects and features will be in part apparent and in part pointed out hereinafter.

BRIEF DESCRIPTION OF THE DRAWINGS

FIG. 1 is a timeline of the clinical course of the patient of Example 1.

DETAILED DESCRIPTION

Figure 2:
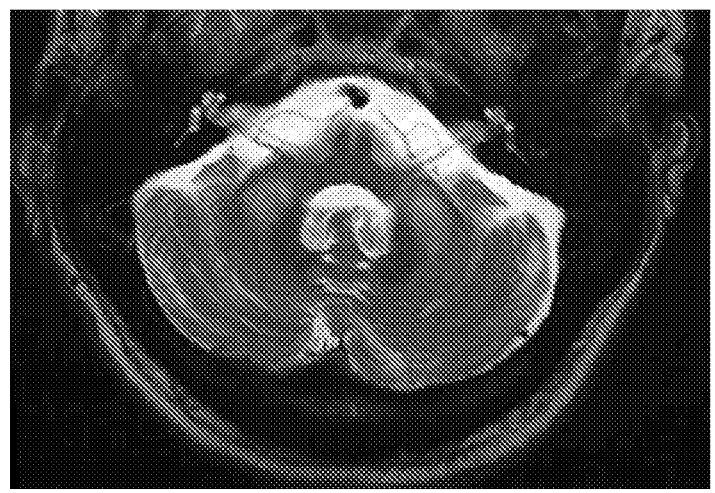
FIG. 2 is a T2 weighted image of the brain of the patient of Example 1. Note the white matter hyperintensities in the middle cerebellar peduncle (MCP) typical of FXTAS.

The present disclosure provides methods for the treatment of certain disease-induced symptoms in a patient, typically a human. In particular, the symptoms are selected from ataxia and non-ataxic imbalance. The disclosure relates, in part, to the discovery that compounds having nicotinic acetylcholine receptor activity (and pharmaceutical compositions including such compounds) may be used to treat ataxia and non-ataxic imbalance stemming from a wide range of underlying diseases. Accordingly, a preferred embodiment of the present disclosure is the use of agents and compounds having nicotinic acetylcholine receptor activity, such as, for example, varenicline, in methods for treating ataxia and non-ataxic imbalance. For example, one embodiment of the present disclosure is directed to method for treating disease-induced ataxia in a human, the method comprising administering to the human a compound having nicotinic acetylcholine receptor activity. Another embodiment of the present disclosure is directed to a method for treating disease-induced non-ataxic imbalance in a human, the method comprising administering to the human a compound having nicotinic acetylcholine receptor activity. In certain of these and other embodiments, the compound administered to the patient is varenicline.

Generally, the compounds having nicotinic acetylcholine receptor activity may have agonistic, antagonistic, and/or modulatory activity. In certain embodiments, the compound having nicotinic acetylcholine receptor activity is a nicotinic acetylcholine receptor agonist. In one preferred embodiment, the compound is varenicline. These and other compounds are used in methods for treating ataxia or non-ataxic imbalance resulting from a range of underlying diseases and medical conditions, including diseases resulting from chronic or long-term exposure to toxins (such as drugs, alcohol, or other agents). The methods comprise administering to the patient the nicotinic acetylcholine receptor-active compound.

As noted above, the methods disclosed herein involve administering to a patient exhibiting ataxic and/or non-ataxic imbalance symptoms, resulting from an underlying disease, a compound having nicotinic acetylcholine receptor activity. In certain embodiments, the patient is administered a pharmaceutical composition comprising the compound; in one particular embodiment, the compound is varenicline. A patient receiving such treatment may exhibit substantial improvement relative to a baseline score calculated or determined prior to treatment. The treatments disclosed herein are also capable of providing a neuroprotective or disease-modifying effect; that is, the treatment involves affecting chemical or biochemical changes in the patient that persist even after treatment is stopped. Without being bound to any particular theory, it is believed that, over time, administration of the compound stabilizes the cell membrane of a neuronal cell and/or helps in the normalization of neuronal cell functions (e.g., the maintenance and recovery of such functions).

The discovery that compounds having nicotinic acetylcholine receptor activity can be used to treat ataxic and other symptoms from a wide range of diseases has clinical significance. Nicotinic acetylcholine receptor-active compounds may be used to treat adverse symptoms of ataxia associated with, for example, Spinocerebellar ataxia, Fragile X/Tremor ataxia syndrome, and Friedreich's ataxia, among a range of others.

One embodiment of the methods of the present disclosure, therefore, comprises administering to a human in need of such treatment a compound having nicotinic acetylcholine receptor activity, typically in the form of a pharmaceutical composition comprising such compound. The compound is generally administered in an effective amount; that is, a dose of sufficient size to have a detectable therapeutic effect on the patient's ataxia and/or non-ataxic imbalance symptoms. The therapeutic effect may be, for instance, any treatment that improves a patient's symptoms or otherwise reduces, alleviates, or minimizes such adverse conditions. In general, therefore, the treatment or treating of the symptoms discussed herein (i.e., ataxia or non-ataxic imbalance) refer to the improvement, amelioration, reduction, or minimization of these symptoms in an individual. It will be appreciated by the person of ordinary skill in the art that a treatment need not be completely effective in reducing or eliminating the symptom(s). Any reduction in the severity of symptoms or delay in the progression of symptoms is desirable to a patient and thus contemplated in the present disclosure. In this regard, it is noted that the methods described herein are not directed to treatment or prophylaxis of the underlying disease, but rather are directed to improving, ameliorating, reducing, or minimizing the subjective indications that characterize the disease (i.e., the symptoms), including physical and physiological manifestations or reactions, and in particular, ataxia and non-ataxic imbalance. The human patient may be, in various embodiments, an infant, child, adolescent, or adult.

Ataxia and Non-Ataxic Imbalance

As noted above, the present disclosure relates to the treatment of ataxia and/or non-ataxic imbalance. In general, a patient's ataxia or non-ataxic imbalance symptoms may be manifested from a disease of any etiology. The ataxia or non-ataxic imbalance may be the major or minor symptom of a wide range of underlying diseases (including pathological disorders or medical conditions). The patient's ataxia and non-ataxic imbalance is disease-induced; that is, it is caused by a disease, as distinguished from drug-induced symptoms of ataxia and non-ataxic imbalance, e.g., resulting from the immediate exposure to drugs or alcohol or other toxins. Additionally or alternatively, underlying diseases manifesting in ataxia and non-ataxic imbalance may be unknown, thus the ataxia and non-ataxic imbalance may also result from idiopathic cases, including those due to anxiety or aging.

Ataxia, including both cerebellar ataxia and spinal ataxia (including posterior spinal ataxia), generally involves the loss or failure of muscular coordination. Patients exhibiting ataxia may have difficulty regulating the force, range, direction, velocity, and rhythm of muscles involved in posture and balance. Ataxia of the trunk muscles, for example, can result in increased postural sway, and an inability to maintain the center of gravity over the base of support. Ataxia and primary or secondary symptoms of ataxic gait and tremor of the extremities, may also lead to manifestations of speech disturbance, dysphagia, abnormal ventilation, and involuntary movements such as dystonia, and sometimes develops into vegetative symptoms or spastic paraplegia, as well as pyramidal or extrapyramidal symptoms, thereby substantially interfering with the activities of daily life.

As noted above, ataxia may result from a wide range of underlying diseases and conditions in a patient, including cerebellar and neurodegenerative disorders and diseases resulting from chronic or long-term exposure to toxins. Symptoms of ataxia may result from a wide range of diseases, disorders, and environmental factors, including infectious diseases, metabolic diseases, neurodegenerative diseases, genetic diseases, vascular diseases, neoplastic diseases, demyelinating diseases, neuromuscular diseases, and diseases resulting from long-term or chronic exposure to toxins (including drugs and alcohol), among a variety of others; in one embodiment, for example, the ataxia is the result of a metabolic disease, a neurodegenerative disease, a vascular disease, a neuromuscular diseases, or a disease resulting from long-term or chronic exposure to toxins.

Diseases, disorders, syndromes, and conditions that may result in ataxic symptoms that may be treated according to the methods described herein include, but are not limited to, amyotrophic lateral sclerosis, benign paroxysmal positional vertigo, cerebellar ataxia type 1 (autosomal recessive), cerebellar ataxias (autosomal recessive), cerebellar ataxias (dominant pure), cerebellar cortical atrophy, cerebellar degeneration (subacute), cerebellar dysfunction, cerebellar hypoplasia, cerebellar hypoplasia (endosteal sclerosis), cerebellar hypoplasia (tapetoretinal degeneration), cerebelloparenchymal autosomal recessive disorder 3, cerebelloparenchymal disorder V, cerebellum agenesis (hydrocephaly), cerebral amyloid angiopathy (familial), cerebral palsy, demyelinating disorder, dorsal column conditions, dysautonomia, dysequilibrium syndrome, dysethesis, endocrine diseases, diseases caused by chronic exposure to toxins (e.g., alcohol, drugs, antiepileptics, neuroleptics), Fragile X/Tremor ataxia syndrome, Friedreich's ataxia, frontal lobe dysfunction, genetic diseases, granulomatous angiitis of the central nervous system, Hallervorden-Spatz disease, Hereditary motor and sensory neuropathy, hydrocephalus (e.g., low or normal pressure), hypotonia, congenital nystagmus, ataxia and abnormal auditory brainstem response, infantile onset spinocerebellar ataxia, Machado-Joseph disease, Meniere's disease, metabolic disorders, Miller Fisher Syndrome, Minamata disease, multiple sclerosis, muscular dystrophy, Myoclonus-ataxia, neurodegenerative diseases, olivopontocerebellar atrophy, paraneoplastic disorders, parkinsonism (atypical), peroneal muscular atrophy, phenyloin toxicity, posterior column ataxia with retinitis pigmentosa, post-polio syndrome, severe damage to the brain (caused by, e.g., head injury, brain surgery, multiple sclerosis or cerebral palsy, chronic alcohol/drug abuse, chronic exposure to toxins, viral infections, or brain tumor), spastic hemiparesis, spastic paraplegia 23, spastic paraplegia glaucoma precocious puberty, SPG, spinocerebellar ataxia, spinocerebellar ataxia (amyotrophy—deafness), spinocerebellar ataxia (dysmorphism), spinocerebellar ataxia 11, spinocerebellar ataxia 17, spinocerebellar ataxia 20, spinocerebellar ataxia 25, spinocerebellar ataxia 29, spinocerebellar ataxia 3, spinocerebellar ataxia (autosomal recessive 1), spinocerebellar ataxia (autosomal recessive 3), spinocerebellar ataxia (autosomal recessive 4), spinocerebellar ataxia (autosomal recessive 5), spinocerebellar ataxia (autosomal recessive, with axonal neuropathy), spinocerebellar ataxia (Machado-Joseph type II), spinocerebellar ataxia (X-linked, 2), spinocerebellar ataxia (X-linked, 3), spinocerebellar ataxia (X-linked, 4), spinocerebellar degenerescence (book type), stroke (e.g., acute or hemorrhagic), vertebral artery dissection, vertebral-basilar insufficiency, and diseases caused by vitamin deficiencies, among a variety of others. In one particular embodiment, the ataxia is the result of a disease selected from Spinocerebellar ataxia, Friedriech's ataxia, and fragile X/tremor ataxia syndrome. In another particular embodiment, the ataxia is the result of Spinocerebellar ataxia or fragile X/tremor ataxia syndrome.

The present invention also relates to the treatment of non-ataxic imbalance. Non-ataxic imbalance generally refers to the loss of balance and impaired coordination and vertigo that is related to the failure of muscular coordination. Like ataxia, symptoms of non-ataxic imbalance may result from a wide range of diseases, disorders, and environmental factors, including infectious diseases, metabolic diseases, neurodegenerative diseases, genetic diseases, vascular diseases, neoplastic diseases, demyelinating diseases, and neuromuscular diseases, among a variety of others; in one embodiment, for example, the non-ataxic imbalance is the result of a metabolic disease, a neurodegenerative disease, a vascular disease, a neuromuscular diseases, or a disease resulting from long-term or chronic exposure to toxins. Particular diseases, disorders, syndromes, and stimuli that may result in non-ataxic imbalance symptoms that may be treated according to the methods described herein include, but are not limited to, acoustic neurinoma, agenesis of the corpus callosum, diseases caused by long-term drug and alcohol abuse, Ataxia Telangiectasia, Angelman syndrome, general balance disorders (e.g., vertigo, falling sensation, unsteadiness, unbalance), brain cancer, cerebral palsy, Chiari Malformation, classic childhood ALD, corticobasal degeneration, herpes zoster oticus, HIV/AIDS, hydrocephalus, multiple sclerosis, muscular dystrophy, olivopontocerebellar atrophy, Parkinson's Disease, atypical parkinsonism, Rett's Syndrome, Shy-Drager Syndrome, stroke, vertigo, Von Hippel-Lindau Disease, Wallenberg's Syndrome, and Wilson's Disease, among a variety of others. In one particular embodiment, the non-ataxic imbalance is the result of a disease selected from Spinocerebellar ataxia, Friedriech's ataxia, and fragile X/tremor ataxia syndrome. In another particular embodiment, the non-ataxic imbalance is the result of Spinocerebellar ataxia or fragile X/tremor ataxia syndrome.

Compounds Having Nicotinic Acetylcholine Receptor Activity

Compounds for treating ataxia or non-ataxic imbalance symptoms according to the methods described herein have nicotinic acetylcholine receptor activity. As noted above, this activity may be agonistic, antagonistic, or modulatory. The compound(s) may have an effect on either the neuronal type nicotinic acetylcholine receptors, the muscle type nicotinic acetylcholine receptor, or both. For example, the compound may be capable of acting on the $\alpha 1$, $\beta 1$, $\delta$, $\gamma$, and $\epsilon$ receptor subunits, and combinations thereof. By way of another example, the compound may be capable of acting on the various homomeric or heteromeric combinations of seventeen different nicotinic receptor subunits: $\alpha 2$ through $\alpha 10$ and $\beta 2$ through $\beta 4$ (e.g., the neuronal subtypes: $(\alpha 4)_3 (\beta 2)_2$, $(\alpha 4)_2 (\beta 2)_3$, and $(\alpha 7)_5$). Generally speaking, this includes, for instance, compounds having activity on Neuronal Type I receptor subunits (e.g., $\alpha 9$, $\alpha 10$), Neuronal Type II receptor subunits (e.g., $\alpha 7$, $\alpha 8$), Neuronal Type III(1) receptor subunits (e.g., $\alpha 2$, $\alpha 3$, $\alpha 4$, and $\alpha 6$), Neuronal Type III(2) receptor subunits (e.g., ($\beta 2$, $\beta 4$), Neuronal Type III(3) receptor subunits (e.g., ($\beta 3$, $\beta 5$), Muscle Type IV receptor subunits (e.g., $\alpha 1$, $\beta 1$, $\delta$, $\gamma$, and $\epsilon$), and combinations thereof.

For example, the compound may be an agonist or partial agonist (including selective agonist or selective partial agonist) of the $\alpha 4\beta 2$ receptor (e.g., ABT-089, ABT-894, cytosine, dianicline (SSR591813), TC-1734, TC-2559, and varenicline, among others). In additional or alternative examples, the compound may be an antagonist of the $\alpha 4\beta 2$ receptor (e.g., anabaseine, DMXB-A, lobeline, mecamylamine, methyllycaconitine, and TC-5214, among others). In another example, the compound may be an antagonist (including non-competitive antagonists) of the $\alpha 3\beta 2$ receptor (e.g., alpha-bungarotoxin, bupropion, fluoxetine, lobeline, and mecamylamine, among others). By way of another example, the compound may be an agonist (including selective agonists) of the $\alpha 7$ receptor (e.g., anabaseine, DMXB-A, galantamine, MEM3454, MEM63908, TC-5214, and varenicline, among others). In another example, the compound may be an antagonist of the $\alpha 7$ receptor (e.g., alpha-bungarotoxin, dihydro-beta-erythroidine, mecamylamine, paroxetine, sertraline, and venlafaxine, among others). In another example, the compound may be an antagonist of the $\alpha 3\beta 4$ receptor (e.g., alpha-bungarotoxin, bupropion, fluoxetine, lobeline, and mecamylamine, among others). By way of another example, the compound may be an antagonist of the $\alpha 3\beta 4$ receptor (e.g., fluoxetine, nefazodone, paroxetine, sertraline, and venlafaxine, among others). By way of yet another example, the compound may have activity (e.g., agonistic, antagonistic, or other activity) on the $\alpha 3\beta 2$, $\alpha 6$, $\beta 2$, $(\alpha 1)2\beta 1\delta\epsilon$ and $(\alpha 1)2\beta 1\delta\gamma$, $\alpha 3$, and/or $\alpha 6\beta 2$ receptors (e.g., varenicline, cytosine, alpha-bungarotoxin, ABT-594, and OmIA, among others).

In some instances, the active agent having nicotinic acetylcholine receptor activity is a known compound with proven clinical efficacy, for example, in smoking cessation. In certain embodiments, the compound is selected from the group consisting of (i) an aryl-fused azapolycyclic compound; (ii) a pyridopyranoazepine; (iii) an aryl-substituted olefinic amine compound; (iv) a benzylidene- or cinnamylidene-anabaseine compound; (v) a heterocyclic ether compound; (vi) 3-pyridyloxyalkyl heterocyclic ether compound; (vii) an N-substituted diazabicyclic compound; (viii) a heterocyclic substituted amino azacycle compound; and (ix) an indazole, benzothioazole, or benzoisothiazole compound. In one embodiment, the compound is selected from the group consisting of ABT-089, ABT-894, alpha-bungarotoxin, anabaseine, bupropion, buspirone, BW284c51, cytisine, dianicline (SSR591813), dihydro-beta-erythoidine, DMXB, DMXB-A (GTS-21), diazoxon, donepezil, exelon, fluoxetine, galantamine, huperzine A, ispronicline (TC-1734/AZD-3480), lobeline, mecamylamine, MEM3454, MEM63908, methyllycaconitine, nefazodone, octanol/ethanol, OmIA, paroxetine, sertraline, tacrine, TC-2559, TC-5214 ((S)-(+)-mecamylamine), TC-5619, tebanicline (ABT-594), varenicline, venlafaxine, XY4083, and combinations thereof. In particular embodiment, the compound is selected from the group consisting of ABT-089, ABT-894, bupropion, cytisine, dianicline (SSR591813), DMXB-A (GTS-21), ispronicline (TC-1734/AZD-3480), lobeline, mecamylamine, methyllycaconitine, TC-2559, TC-5214 ((S)-(+)-mecamylamine), tebanicline (ABT-594), varenicline, and combinations thereof. In another particular embodiment, the compound is selected from the group consisting of donepezil, exelon, fluoxetine, galantamine, huperzine A, MEM3454, MEM63908, tacrine, XY4083, and combinations thereof. In a preferred embodiment, the compound is selected from the group consisting of varenicline, dianicline, ispronicline, and combinations thereof; more preferably in this embodiment, the compound is varenicline.

In one particular embodiment, the compound is an aryl-fused azapolycyclic compound. According to this embodiment, for example, the compound administered to the patient may have the formula (i):

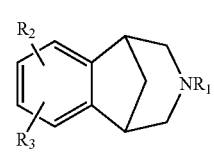

(i)

wherein $R_1$ is hydrogen, $(C_1-C_6)$alkyl, unconjugated $(C_3-C_6)$alkenyl, benzyl, XC(=O)$R_{13}$ or —CH$_2$CH$_2$—O—$(C_1-C_4)$alkyl;

$R_2$ and $R_3$ are selected, independently, from hydrogen, $(C_2-C_6)$alkenyl, $(C_2-C_6)$alkynyl, hydroxy, nitro, amino, halo, cyano, —SO$_q$(C$_1$-C$_6$)alkyl wherein q is zero, one or two, (C$_1$-C$_6$)alkylamino-, [(C$_1$-C$_6$)alkyl]$_2$amino-, —CO$_2$R$_4$, —CONR$_5$R$_6$, —SO$_2$NR$_7$R$_8$, —C(=O)R$_{13}$, —XC(=O)R$_{13}$, aryl-(C$_0$-C$_3$)alkyl- or aryl-(C$_0$-C$_3$)alkyl-O—, wherein said aryl is selected from phenyl and naphthyl, heteroaryl-(C$_0$-C$_3$)alkyl- or heteroaryl-(C$_0$-C$_3$)alkyl-O—, wherein said heteroaryl is selected from five to seven membered aromatic rings containing from one to four heteroatoms selected from oxygen, nitrogen and sulfur, and X$_2$(C$_0$-C$_6$)alkoxy-(C$_0$-C$_6$)alkyl-, wherein X$_2$ is absent or X$_2$ is (C$_1$-C$_6$)alkylamino- or [(C$_1$-C$_6$)alkyl]$_2$amino-, and wherein the (C$_0$-C$_6$)alkoxy-(C$_0$-C$_6$)alkyl- moiety of said X$_2$(C$_0$-C$_6$)alkoxy-(C$_0$-C$_6$)alkyl- contains at least one carbon atom, and wherein from one to three of the carbon atoms of said (C$_0$-C$_6$)alkoxy-(C$_0$-C$_6$)alkyl- moiety may optionally be replaced by an oxygen, nitrogen or sulfur atom, with the proviso that any two such heteroatoms must be separated by at least two carbon atoms, and wherein any of the alkyl moieties of said (C$_0$-C$_6$)alkoxy-(C$_0$-C$_6$)alkyl- may be optionally substituted with from two to seven fluorine atoms, and wherein one of the carbon atoms of each of the alkyl moieties of said aryl-(C$_0$-C$_3$)alkyl- and said heteroaryl-(C$_0$-C$_3$)alkyl- may optionally be replaced by an oxygen, nitrogen or sulfur atom, and wherein each of the foregoing aryl and heteroaryl groups may optionally be substituted with one or more substituents, preferably from zero to two substituents, independently selected from (C$_1$-C$_6$)alkyl optionally substituted with from one to seven fluorine atoms, (C$_1$-C$_6$)alkoxy optionally substituted with from two to seven fluorine atoms, halo (e.g., chloro, fluoro, bromo or iodo), (C$_2$-C$_6$)alkenyl, (C$_2$-C$_6$)alkynyl, hydroxy, nitro, cyano, amino, (C$_1$-C$_6$)—, [(C$_1$-C$_6$)alkyl]$_2$amino-, —CO$_2$R$_4$, —CONR$_5$R$_6$, —SO$_2$NR$_7$R$_8$, —C(=O)R$_{13}$ and —XC(=O)R$_{13}$; or R$_2$ and R$_3$, together with the carbons to which they are attached, form a four to seven membered monocyclic, or a ten to fourteen membered bicyclic, carbocyclic ring that can be saturated or unsaturated, wherein from one to three of the nonfused carbon atoms of said monocyclic rings, and from one to five of the carbon atoms of said bicyclic rings that are not part of the benzo ring shown in formula (i), may optionally and independently be replaced by a nitrogen, oxygen or sulfur, and wherein said monocyclic and bicyclic rings may optionally be substituted with one or more substituents, preferably from zero to two substituents for the monocyclic rings and from zero to three substituents for the bicyclic rings, that are selected, independently, from (C$_0$-C$_6$)alkoxy-(C$_0$-C$_6$)alkyl-, wherein the total number of carbon atoms does not exceed six and wherein any of the alkyl moieties may optionally be substituted with from one to seven fluorine atoms; nitro, oxo, cyano, halo, (C$_2$-C$_6$)alkenyl, (C$_2$-C$_6$)alkynyl, hydroxy, amino, (C$_1$-C$_6$)alkylamino-, [(C$_1$-C$_6$)alkyl]$_2$amino-, —CO$_2$R$_4$, —CONR$_5$R$_6$, —SO$_2$NR$_7$R$_8$, —C(=O)R$_{13}$, and —XC(=O)R$_{13}$;

each R$_4$, R$_5$, R$_6$, R$_7$, R$_8$ and R$_{13}$ is selected, independently, from hydrogen and (C$_1$-C$_6$) alkyl, or R$_5$ and R$_6$, or R$_7$ and R$_8$ together with the nitrogen to which they are attached, form a pyrrolidine, piperidine, morpholine, azetidine, piperazine, —N—(C$_1$-C$_6$)alkylpiperazine or thiomorpholine ring, or a thiomorpholine ring wherein the ring sulfur is replaced with a sulfoxide or sulfone; and each X is, independently, (C$_1$-C$_6$)alkylene: with the proviso that: (a) at least one of R$_1$, R$_2$ and R$_3$ must be the other than hydrogen, and (b) when R$_2$ and R$_3$ are hydrogen, R$_1$ cannot be methyl or hydrogen; and the pharmaceutically acceptable salts of such compounds.

In a particular embodiment, R$_1$, R$_2$, and R$_3$ are each hydrogen; more preferably in this embodiment, the compound has the formula:

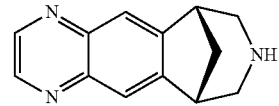

This compound 7,8,9,10-tetrahydro-6,10-methano-6H-pyrazino (2,3-h)(3) benzazepine (also known as varenicline or Chantix®) is approved as a medication for the treatment nicotine dependence. Compounds corresponding to formula (i) and varenicline are described in further detail in International Publication No. WO2001/062736; U.S. Pat. No. 6,410,550; U.S. Pat. No. 6,605,610; U.S. Pat. No. 6,890,927; and U.S. Pat. No. 7,265,119 (each of which is hereby incorporated by reference herein in its entirety). In a particular embodiment, the compound administered to the patient is varenicline.

In another particular embodiment, the compound is a pyridopyranoazepine. According to this embodiment, for example, the compound administered to the patient may have the formula (ii):

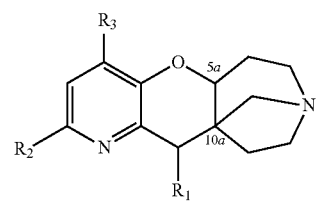

wherein R$_1$ is a hydrogen atom, a (C$_1$-C$_4$)alkyl group, a phenyl(C$_1$-C$_4$)alkyl group, a phenylhydroxy(C$_1$-C$_4$)alkyl group, a furanyl(C$_1$-C$_4$)alkyl group, or a furanyl-hydroxy (C$_1$-C$_4$)alkyl group, R$_2$ is either a hydrogen or halogen atom or a trifluoromethyl, cyano, hydroxyl, nitro, acetyl, (C$_1$-C$_6$) alkyl or (C$_1$-C$_6$)alkoxy group or a group of general formula NR$_4$R$_5$ in which R$_4$ is a hydrogen atom or a (C$_1$-C$_4$)alkyl or (C$_1$-C$_4$)alkanoyl group and R$_5$ is a hydrogen atom or a (C$_1$-C$_4$)alkyl group, or else R$_4$ and R$_5$ form, with the nitrogen atom which carries them, a C$_4$-C$_7$ ring, or a phenyl or naphthyl group optionally substituted by a halogen atom or a trifluoromethyl, trifluoromethoxy, cyano, hydroxyl, nitro, acetyl, (C$_1$-C$_6$)alkyl, (C$_1$-C$_6$)alkoxy or methylenedioxy group linked in the 2 and 3 positions of the phenyl ring, and R$_3$ is a hydrogen or halogen atom or a (C$_1$-C$_4$)alkyl group.

The compounds of general formula (ii) can exist in the state of bases or of addition salts to acids. In addition, the atoms in positions 5a and 10a being asymmetric, a compound can exist in the form of pure geometric and optical isomers or of mixtures of the latter. In a particular embodiment, R$_1$, R$_2$, and R$_3$ are each hydrogen; more preferably in this embodiment, the compound has the formula:

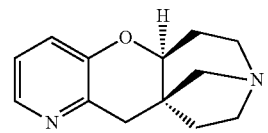 [SMILES: c1cnc2c(c1)O[C@H]1CCN3CC[C@@]1(C2)C3]

This compound (5aS,8S,10aR)-5a,6,9,10-Tetrahydro, 7H,11H-8,10a-methanopyrido[2',3':5,6]pyrano[2,3-d] azepine (also known as SSR-591,813 or dianicline) is presently in clinical trials as a medication for the treatment nicotine dependence. Compounds corresponding to formula (ii) and dianicline (SSR591813) are described in further detail in U.S. Pat. No. 6,538,003 (hereby incorporated by reference herein in its entirety).

In another particular embodiment, the compound is an aryl-substituted olefinic amine compound. According to this embodiment, for example, the compound administered to the patient may have the formula (iii):

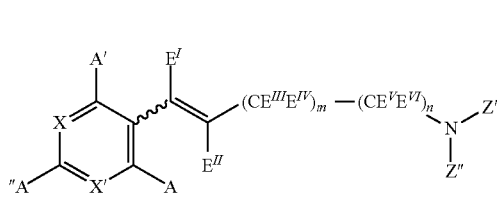

where each of X and X' are individually nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991); m is an integer and n is an integer such that the sum of m plus n is 1, 2, 3, 4, 5, 6, 7, or 8, preferably is 1, 2, or 3, and most preferably is 2 or 3; the wavy line in the structure indicates that the compound can have the cis (Z) or trans (E) form; $E^I$, $E^{II}$, $E^{III}$, $E^{IV}$, $E^V$ and $E^{VI}$ individually represent hydrogen or lower alkyl (e.g., straight chain or branched alkyl including $C_1$-$C_8$, preferably $C_1$-$C_5$, such as methyl, ethyl, or isopropyl) or halo substituted lower alkyl (e.g., straight chain or branched alkyl including $C_1$-$C_8$, preferably $C_1$-$C_5$, such as trifluoromethyl or trichloromethyl), and at least one of $E^I$, $E^{II}$, $E^{III}$, $E^{IV}$, $E^V$ and $E^{VI}$ is non-hydrogen and the remaining $E^I$, $E^{II}$, $E^{III}$, $E^{IV}$, $E^V$ and $E^{VI}$ are hydrogen; and Z' and Z" individually represent hydrogen or lower alkyl (e.g., straight chain or branched alkyl including $C_1$-$C_8$ preferably $C_1$-$C_5$, such as methyl, ethyl, or isopropyl), and preferably at least one of Z and Z" is hydrogen, and most preferably Z' is hydrogen and Z" is methyl; alternatively Z' is hydrogen and Z" represents a ring structure (cycloalkyl or aromatic), such as cyclopropyl, cyclobutyl, cyclopentyl, cyclohexyl, cycloheptyl, adamantyl, quinuclidinyl, pyridyl, quinolinyl, pyrimidinyl, phenyl, benzyl (where any of the foregoing can be suitably substituted with at least one substituent group, such as alkyl, halo, or amino substituents); alternatively Z', Z", and the associated nitrogen atom can form a ring structure such as aziridinyl, azetidinyl, pyrollidinyl, piperidinyl, quinuclidinyl, piperazinyl, or morpholinyl.

Representative compounds having the generic structure (iii) include (4E)-N-methyl-5-(3-pyridyl)-4-pen-ten-2-amine, (4E)-N-methyl-5-(5-pyrimidinyl)-4-penten-2-amine, (4E)-N-methyl-5-(5-methoxy-3-pyridyl)-4-penten-2-amine, (4E)-N-methyl-5-(6-amino-5-methyl-3-pyridyl)-4-penten-2-amine, (2R)-(4E)-N-methyl-5-(3-pyridyl)-4-penten-2-amine, (2R)-(4E)-N-methyl-5-(5-isopropoxy-3-pyridyl)-4-penten-2-amine, (4E)-N-methyl-5-(5-bromo-3-pyridyl)-4-penten-2-amine, (4E)-N-methyl-5-(5-ethoxy-3-pyridyl)-4-penten-2-amine, (2S)-(4E)-N-methyl-5-(3-pyridyl)-4-penten-2-amine, (4E)-N-methyl-5-(5-isopropoxy-3-pyridyl)-4-penten-2-amine and (2S)-(4E)-N-methyl-5-(5-isopropoxy-3-pyridyl)-4-penten-2-amine (also known as ispronicline, TC-1734, or AZD-3480). Compounds corresponding to formula (iii) are described in further detail in International Publication WO 99/65876 and WO 00/75710; U.S. Patent Application Publication 2002/0052497; U.S. Pat. No. 6,979,695; and U.S. Pat. No. 7,045,538 (each of which is hereby incorporated by reference herein in its entirety).

In another particular embodiment, the compound is a benzylidene- or cinnamylidene-anabaseine compound. According to this embodiment, for example, the compound administered to the patient may have the formula (iv):

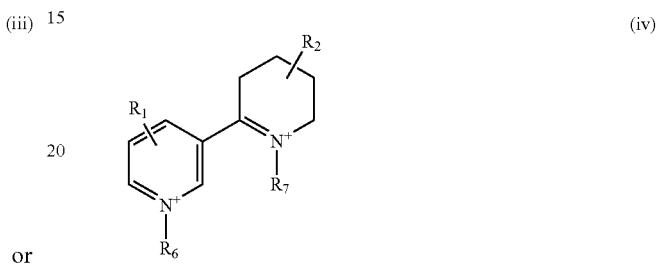

or a salt thereof, wherein $R_1$, $R_6$ and $R_7$ are hydrogen or $C_1$-$C_4$ alkyl; and $R_2$ is =CHCH=CHX, wherein X is

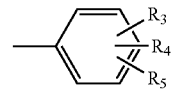

wherein $R_3$, $R_4$, and $R_5$ are selected from the group consisting of hydrogen, $C_1$-$C_4$ alkyl optionally substituted with N,N-dialkylamino having 1 to 4 carbon atoms in each of the alkyls, $C_1$-$C_6$ alkoxy optionally substituted with N,N-dialkylamino having 1 to 4 carbons in each of the alkyls, carboalkoxy having 1 to 4 carbons in the alkoxy (such as acetoxy), amino, amido having 1 to 4 carbons in the acyl (such as acetylamino), cyano, N,N-dialkylamino having 1 to 4 carbons in each of the alkyls, halo, hydroxyl, and nitro.

Representative cinnamylidene-anabaseines having the generic structure (iv) include, but are not limited to, 3-(4-acetylaminocinnamylidene) anabaseine, 3-(4-hydroxycinnamylidene)anabaseine, 3-(4-methoxycinnamylidene)anabaseine, 3-(4-hydroxy-2-methoxycinnamylidene) anabaseine, 3-(2,4-dimethoxycinnamylidene)anabaseine, and 3-(4-acetoxycinnamylidene)anabaseine. Representative benzylidene-anabaseines having the generic structure (iv) include, but are not limited to, 3-(2,4-dimethoxybenzylidene)anabaseine (also known as DMXB-A and GTS-21), 3-(4-hydroxybenzylidene)anabaseine, 3-(4-methoxybenzylidene)anabaseine, 3-(4-aminobenzylidene) anabaseine, 3-(4-hydroxy-2-methoxybenzylidene)anabaseine, 3-(2-hydroxy-4-methoxybenzylidene)anabaseine, 3-(4-isopropoxybenzylidene)anabaseine, and (7'-methyl-3-(2,4-dimethoxybenzylidene)). Compounds corresponding to formula (iv) are described in further detail in International Publication WO 99/10338 and WO 2006/133303; U.S. Pat. No. 5,741,802; and U.S. Pat. No. 5,977,144 (each of which is hereby incorporated by reference herein in its entirety).

In another particular embodiment, the compound is a heterocyclic ether compound. According to this embodiment, for example, the compound administered to the patient may have the formula (v):

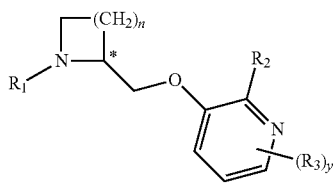

(v)

wherein the asterisk indicates a chiral center; n is 1, 2, or 3; y is 1 or 2; $R_1$ is H, allyl or $C_1$-$C_6$-alkyl; $R_2$ is H, F, Cl, or $C_1$-$C_3$-alkyl; and $R_3$ is independently selected from H, F, Cl, Br or $C_1$-$C_6$-alkyl; with the provisos that (a) when $R_2$ is $C_1$-$C_3$-alkyl, then $R_1$ is H, and (b) when y is 2, then $R_2$ is hydrogen.

Representative heterocyclic ethers having the generic structure (v) include, but are not limited to, 3-(2-(S)-azetidinylmethoxy)pyridine; 3-((1-methyl-2-S)-azetidinyl)methoxy)pyridine; 2-methyl-3-(2-(S)-azetidinylmethoxy)pyridine (also known as ABT-089); 5-chloro-3-(2-(S)-azetidinylmethoxy)pyridine; 5-([(2R)-azetidin-2-yl]methoxy)-2-chloropyridine (also known as tebanicline or ABT-594); 6-methyl-3-(2-(S)-azetidinylmethoxy)pyridine; 3-(2-(S)-azetidinylmethoxy)chloropyridine; 3-(2-(R)-azetidinylmethoxy)pyridine; 3-((1-methyl-2-(R)-azetidinyl)methoxy)pyridine; 3-(2-(S)-azetidinylmethoxy)-5-bromopyridine; 3-((1-methyl-2-(S)-azetidinyl)methoxy)-5-bromopyridine; and 5,6-dichloro-3-(2-(S)-azetidinylmethoxy)pyridine; 3-(2-(R)-pyrrolidinylmethoxy)pyridine; 3-(2-(S)-pyrrolidinylmethoxy)pyridine; 5-chloro-3-(2-(S)-pyrrolidinylmethoxy)pyridine; 2-methyl-3-(2-(S)-pyrrolidinylmethoxy)pyridine; 6-methyl-3-(2-(S)-pyrrolidinylmethoxy)pyridine; 5-chloro-3-(2-(R)-pyrrolidinylmethoxy)pyridine; 6-methyl-3-(2-(R)-pyrrolidinylmethoxy)pyridine; 3-(2-(S)-pyrrolidinylmethoxy)-6-chloropyridine; 5-bromo-3-(2-(S)-pyrrolidinylmethoxy)pyridine; 3-((1-methyl-2-(S)-pyrrolidinyl)methoxy)pyridine; 5-chloro-3-(1-methyl-2-(S)-pyrrolidinyl)methoxy)pyridine; 6-methyl-3-((1-methyl-2-(S)-pyrrolidinyl)methoxy)pyridine; 5-bromo-3-((1-methyl-2-(S)-pyrrolidinyl)methoxy)pyridine; 6-chloro3-((1-methyl-2-(S)-pyrrolidinyl)methoxy)pyridine; 5-n-butyl-3-((1-methyl-2-(S)-pyrrolidinyl)methoxy)pyridine; 5-n-propyl-3-((1-methyl-2-(S)-pyrrolidinyl)methoxy)pyridine; 5-methyl-3-(1-methyl-2-(S)-pyrrolidinylmethoxy)pyridine; and 5-ethyl-3-(1-methyl-2-(S)-pyrrolidinylmethoxy)pyridine; or a pharmaceutically-acceptable salt or prodrug thereof. Compounds corresponding to formula (v) are described in further detail in International Publication WO 99/32480; U.S. Pat. No. 5,914,328; and U.S. Pat. No. 5,948,793 (each of which is hereby incorporated by reference herein in its entirety).

In another particular embodiment, the compound is a 3-pyridyloxyalkyl heterocyclic ether compound. According to this embodiment, for example, the compound administered to the patient may have the formula (vi):

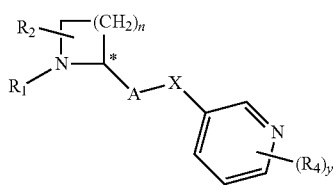

(vi)

wherein the asterisk indicates a chiral center; n is an integer selected from 1, 2, or 3; X is oxygen or sulfur; $R_1$ is H, allyl or $C_1$-$C_6$-alkyl; $R_2$ is hydrogen, or when n=2, is a single substituent selected from the group consisting of —$CH_2OH$, —$CH_2F$, —$CH_2CN$, —$CH_2OCH_3$, —Br, —Cl, —F, —OH, —CH, —($C_1$-$C_3$ alkoxyl), —$OCOCH_3$, and O-methanesulfonyl, with the proviso that when $R_2$ is substituted at the 3-position or the 5-position of the pyrrolidinyl ring, it is a $C_1$-$C_3$ group; A is selected from the group consisting of:

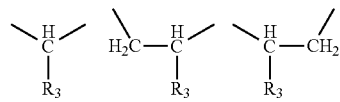

where $R_3$ is H or $C_1$-$C_6$ alkyl; y is 1, 2, or 3 with the provisos that a) when y=1, $R_4$ is selected from the group consisting of (i) a single substituent at the 2-position of the pyridine ring selected from chlorine and fluorine, and (ii) a single substituent substituted at the 5- or 6-position of the pyridine ring selected from the group consisting of —CN, —$CF_3$, —$NO_2$, —$CH_2OH$, —$CH_2CN$, —$NH_2$, —NH—CHO, —NHCO($C_1$-$C_3$ alkyl), —N($C_1$-$C_3$ alkyl)-CO($C_1$-$C_3$ alkyl), —NH—($C_1$-$C_3$ alkyl), —N($C_1$-$C_3$ alkyl)$_2$, —COOH, —COO($C_1$-$C_3$ alkyl), —$CONH_2$, —CONH($C_1$-$C_3$ alkyl), —CONHbenzyl, and —OCO($C_1$-$C_3$-alkyl); b) when y=2, $R^4$ is substituted at the 2,5-, 2,6- or 5,6-positions of the pyridine ring wherein the 2-position substituent is selected from the group consisting of —Br, —Cl, —F, —OH, —($C_1$-$C_4$ alkyl) and —($C_1$-$C_3$ alkoxy) and the substituents at the 5- or 6-positions of the pyridine ring are selected from the group consisting of —Br, —Cl, —F, —OH, —($C_1$-$C_4$ alkyl), —CN, —$CF_3$, —$NO_2$, —$CH_2OH$, —$CH_2CN$, alkoxy), —$NH_2$, —NH—CHO, —NHCO($C_1$-$C_3$ alkyl), —N($C_3$-$C_3$ alkyl)CO($C_1$-$C_3$ alkyl), —NH—($C_1$-$C_3$ alkyl), —N($C_1$-$C_3$ alkyl)$_2$, —COOH, —COO($C_1$-$C_3$ alkyl), —$CONH_2$, —CONH—($C_1$-$C_3$ alkyl), —CONHbenzyl, and —OCO($C_1$-$C_3$ alkyl); and c) when y=3, $R_4$ is a substituent at the 2-position of the pyridine ring selected from the group consisting of —Br, —Cl, —F, —OH, —$C_1$-$C_4$ alkyl, and —$C_1$-$C_3$ alkoxy; and second and third substituents at the 5- and 6-position of the pyridine ring are independently selected from the group consisting of —Br, —Cl, —F, —OH, —$C_1$-$C_4$ alkyl, —CN, —$CF_3$, —$NO_2$, —$CH_2OH$, —$CH_2CN$, —($C_1$-$C_3$ alkoxy), —$NH_2$, —NH—CHO, —NHCO($C_1$-$C_3$ alkyl), —N($C_1$-$C_3$ alkyl)CO($C_1$-$C_3$ alkyl), —NH—($C_1$-$C_3$alkyl), —N($C_1$-$C_3$-alkyl)$_2$, —COOH, —COO($C_1$-$C_3$-alkyl), —$CONH_2$, —CONH($C_3$-$C_3$ alkyl), —CONHbenzyl, and —OCO($C_1$-$C_3$ alkyl).

Compounds corresponding to formula (vi) are described in further detail in International Publication WO 96/040682 (hereby incorporated by reference herein in its entirety).

In another particular embodiment, the compound is a N-substituted diazabicyclic compound. According to this embodiment, for example, the compound administered to the patient may have the formula (vii):

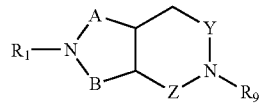

(vii)

or pharmaceutically acceptable salts and prodrugs thereof, wherein A is selected from the group consisting of a covalent bond, $CH_2$, $CH_2CH_2$, and $CH_2CH_2CH_2$; B is selected from the group consisting of $CH_2$ and $CH_2CH_2$, provided that when A is $CH_2CH_2CH_2$, then B is $CH_2$; Y is selected from the group consisting of a covalent bond, $CH_2$, and $CH_2CH_2$; Z is selected from the group consisting of a covalent bond, $CH_2$, and $CH_2CH_2$, provided that when Y is $CH_2CH_2$, then Z is a covalent bond and further provided that when Z is $CH_2CH_2$, then Y is a covalent bond;

$R_1$ is selected from the group consisting of:

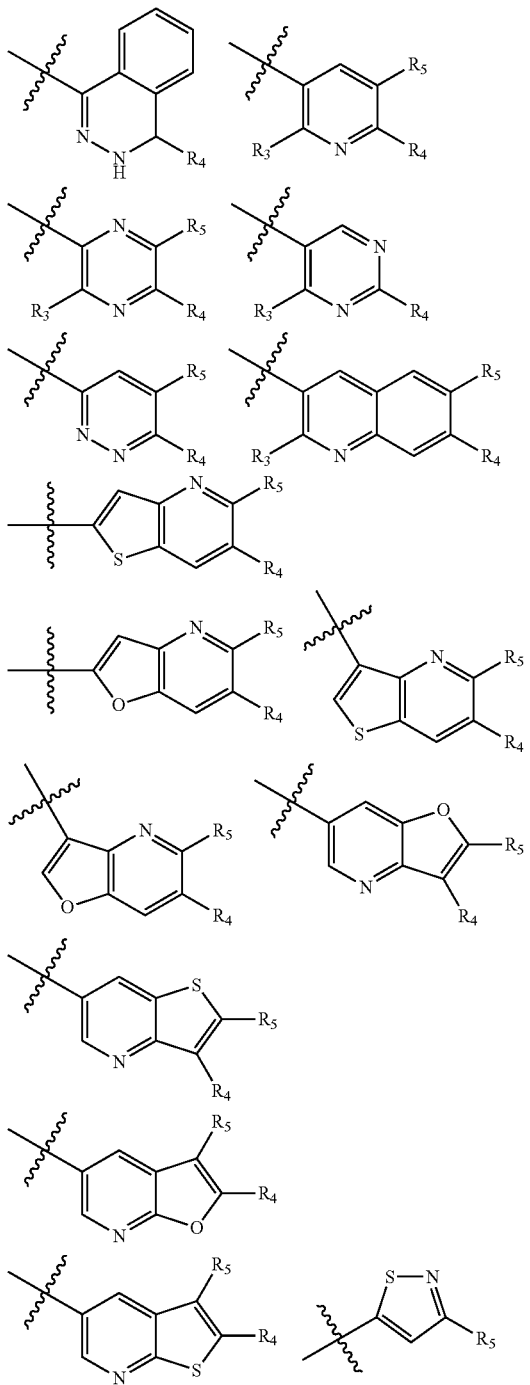

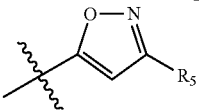

$R_3$ is selected from the group consisting of hydrogen, alkyl, and halogen;

$R_4$ is selected from the group consisting of hydrogen, alkoxy, alkyl, amino, halogen, and nitro;

$R_5$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, —$NR_6S(O)_2R_7$, —$C(NR_6)NR_7R_8$, —$CH_2C(NR_6)NR_7R_8$, —$C(NOR_6)R_7$, —$C(NCN)R_6$, —$C(NNR_6R_7)R_8$, —$S(O)_2OR_6$, and —$S(O)_2R_6$;

$R_6$, $R_7$, and $R_8$ are independently selected from the group consisting of hydrogen and alkyl;

and $R_9$ is selected from the group consisting of hydrogen, alkoxycarbonyl, alkyl, amino, aminoalkyl, aminocarbonylalkyl, benzyloxycarbonyl, cyanoalkyl, dihydro-3-pyridinylcarbonyl, hydroxy, hydroxyalkyl, and phenoxycarbonyl.

Representative heterocyclic ethers having the generic structure (vii) include, but are not limited to, (1R,5R)-6-(6-chloro-3-pyridinyl)-2,6-diazabicyclo[3.2.0]heptane; (1R,5R)-6-(3-pyridinyl)-2,6-diazabicyclo[3.2.0]heptane; (cis)-6-(3-pyridinyl)-3,6-diazabicyclo[3.2.0]heptane; (cis)-6-(6-chloro-3-pyridinyl)-3,6-diazabicyclo[3.2.0]heptane; (1R,5S)-6-(3-pyridinyl)-3,6-diazabicyclo[3.2.0]heptane; (1R,5S)-6-(5-bromo-3-pyridinyl)-3,6-diazabicyclo[3.2.0]heptane; (1S,5R)-6-(6-chloro-3-pyridinyl)-3,6-diazabicyclo[3.2.0]heptane; (1S,5R)-6-(3-pyridinyl)-3,6diazabicyclo[3.2.0]heptane; (1R,5S)-6-(6-chloro-3-pyridinyl)-3,6-diazabicyclo[3.2.0]heptane; (1S,5R)-6-(5-ethynyl-3-pyridinyl)-3,6-diazabicyclo[3.2.0]heptane; (1S,5R)-6-(5-vinyl-3-pyridinyl)-3,6-diazabicyclo[3.2.0]heptane; 5-[(1S,5R)-3,6-diazabicyclo[3.2.0]hept-6-yl]nicotinonitrile; (1S,5R)-6-(5-bromo-3-pyridinyl)-3,6-diazabicyclo[3.2.0]heptane; (1S,5R)-6-(6-bromo-5-vinyl-3-pyridinyl)-3,6-diazabicyclo[3.2.0]heptane; 2-bromo-5-[(1R,5S)-3,6-diazabicyclo[3.2.0]hept-6-yl]nicotinonitrile; (1R,5S)-6-(5-ethynyl-3-pyridinyl)-3,6-diazabicyclo[3.2.0]heptane; 5-[(1R,5S)-3,6-diazabicyclo[3.2.0]hept-6-yl]nicotinonitrile; (cis)-8-(3-pyridinyl)-3,8-diazabicyclo[4.2.0]octane; (cis)-8-(6-chloro-3-pyridinyl)-3,8-diazabicyclo[4.2.0]octane; (1S,6R) (cis)-8-(6-chloro-3-pyridinyl)-3,8-diazabicyclo[4.2.0]octane; (–) (cis)-8-(6-chloro-3-pyridinyl)-3,8-diazabicyclo[4.2.0]octane; 5-[(1R,6S)-3,8-diazabicyclo[4.2.0]oct-8-yl]nicotinonitrile; (1S,6R)-5-[3,8-diazabicyclo[4.2.0]oct-8-yl]nicotinonitrile; (1R,5S)-6-(5,6-dichloro-3-pyridinyl)-3,6-diazabicyclo[3.2.0]heptane; (1S,5R)-6-(5,6-dichloro-3-pyridinyl)-3,6-diazabicyclo[3.2.0]heptane; (cis)-6-(5,6-dichloro-3-pyridinyl)-3,6-diazabicyclo[3.2.0]heptane; (cis)-8-(5-methoxy-3-pyridinyl)-3,8-diazabicyclo[4.2.0]octane; (1R,5S)-6-(5-methoxy-3-pyridinyl)-3,6-diazabicyclo[3.2.0]heptane; (1S,5R)-6-(5-methoxy-3-pyridinyl)-3,6-diazabicyclo[3.2.0]heptane; (cis)-6-(6-bromo-5-methoxy-3-pyridinyl)-3,6diazabicyclo[3.2.0]heptane; (1R,5S)-6-(6-chloro-5-methyl-3-pyridinyl)-3,6-diazabicyclo[3.2.0]heptane; (1S,5R)-6-(6-chloro-5-methyl-3-pyridinyl)-3,6-diazabicyclo[3.2.0]heptane; (1S,6R) (cis)-8-(5-methoxy-3-pyridinyl)-3,8-diazabicyclo[4.2.0]octane; (1R,6S)-8-(5-methoxy-3- pyridinyl)-3,8-diazabicyclo[4.2.0]octane; (cis)-8-(6-chloro-5-methyl-3-pyridinyl)-3,8-diazabicyclo[4.2.0]octane; (1S,6R)-8-(6-chloro-5-methyl-3-pyridinyl)-3,8-diazabicyclo[4.2.0]octane; (1R,6S)-8-(6-chloro-5-methyl-3-pyridinyl)-3,8-diazabicyclo[4.2.0]octane; (1S,6R)-8-(3-pyridinyl)-3,8-diazabicyclo[4.2.0]octane; (1R,6S)-8(3-pyridinyl)-3,8-diazabicyclo[4.2.0]octane; (cis)-8-(5,6-dichloro-3-pyridinyl)-3,8-diazabicyclo[4.2.0]octane (1S,6R)-8-(5,6-dichloro-3-pyridinyl)-3,8-diazabicyclo[4.2.0]octane; (1R,6S)-8-(5,6-dichloro-3-pyridinyl)-3,8-diazabicyclo[4.2.0]octane; (cis)-6-(6-bromo-5-methoxy-3-pyridinyl)-3,6-diazabicyco[3.2.0]heptane; (1R,5S)-6-(6-bromo-5-methoxy-3-pyridinyl)-3,6-diazabicyclo[3.2.0]heptane; (1S,5R)-6-(6-bromo-5-methoxy-3-pyridinyl)-3,6-diazabicyclo[3.2.0]heptane; (cis)-6-(5-azido-3-pyridinyl)-3,6-diazabicylo[3.2.0]heptane; (1R,5S)-6-(5-azido-3-pyridinyl)-3,6-diazabicyclo[3.2.0]heptane; and (1R,5S)-6-(5-azido-3-pyridinyl)-3,6-diazabicyclo[3.2.0]heptane. Compounds corresponding to formula (vii) are described in further detail in International Publication WO 2004/0186107; and U.S. Pat. No. 6,809,105 (each of which is hereby incorporated by reference herein in its entirety).

In another particular embodiment, the compound is a heterocyclic substituted amino azacycle compound. According to this embodiment, for example, the compound administered to the patient may have the formula (viii):

Z—R₃ (viii)

wherein Z is selected from the group consisting of:

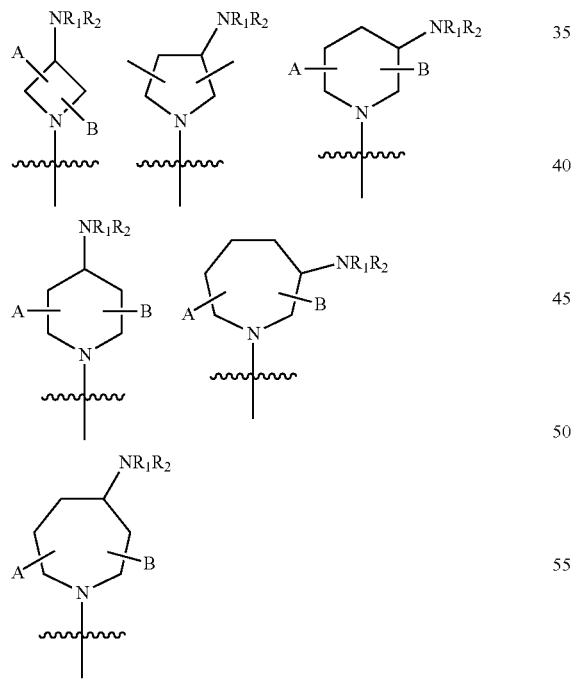

$R_1$ and $R_2$ are independently selected from the group consisting of hydrogen and alkyl; A and B are independently absent or independently selected from the group consisting of alkenyl, alkoxy, alkoxycarbonyl, alkyl, alkynyl, carboxy, haloalkyl, halogen, hydroxyl, and hydroxyalkyl; $R_3$ is selected from the group consisting of:

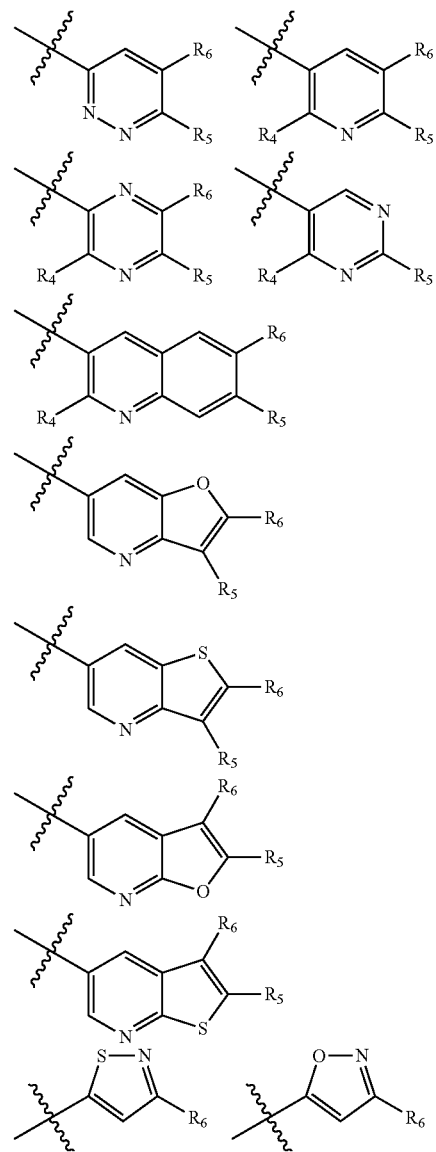

$R_4$ is selected from the group consisting of hydrogen, alkyl, and halogen; $R_5$ is selected from the group consisting of hydrogen, alkyl, halogen, nitro, and —$NR_{10}R_{11}$, wherein $R_{10}$ and $R_{11}$ are independently selected from the group consisting of hydrogen and lower alkyl; $R_6$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxyl, hydroxyalkyl, mercapto, mercaptoalkyl, nitro, 5-tetrazolyl, —$NR_7SO_2R_8$, —$C(NR_7)NR_8R_9$, —$CH_2C(NR_7)NR_8R_9$, —$C(NOR_7)R_8$, —$C(NCN)R_7$, —$C(NNR_7R_8)R_9$, —$S(O)_2OR_7$, and —$S(O)_2R_7$; and $R_7$, $R_8$, and $R_9$ are independently selected from the group consisting of hydrogen and alkyl; provided that when $R_3$ is pyridazine then $R_1$ is alkyl.

Representative compounds of formula (viii) include, but are not limited to: N-[(3S)-1-(6-chloro-3-pyridinyl)pyrrolidinyl]-N-methylamine; (3S)-1-(6-chloro-3-pyridinyl)pyrrolidinylamine; N-[(3S)-1-(6-chloro-3-pyridinyl)pyrrolidinyl]-N,N-dimethylamine; (3R)-1-(6-chloro-3-pyridinyl)pyrrolidinylamine; N-[(3R)-1-(6-chloro-3-pyridinyl)pyrrolidinyl]-N-methylamine; N-[(3R)-1-(6-chloro-3-pyridinyl)pyrrolidinyl]-N,N-dimethylamine; 1-(6-chloro-3-pyridinyl)-3-pyrrolidinylamine; (3S)-1-(3-pyridinyl)pyrrolidinylamine; N-methyl-N-[(3S)-1-(3-pyridinyl)pyrrolidinyl]amine; 1-(3-pyridinyl)-3-pyrrolidinylamine; (3R)-1-[5-(trifluoromethyl)-3-pyridinyl]pyrrolidinylamine; N-methyl-N-{(3R)1-[5-(trifluoromethyl)-3-pyridinyl]pyrrolidinyl}amine; (3S)-1-[5-(trifluoromethyl)-3-pyridinyl]pyrrolidinylamine; N-methyl-N-{(3S)-1-[5-(tri fluoromethyl)-3-pyridinyl]pyrrolidinyl}amine; (3R)-1-(6-chloro-5-chloro-5-methyl-3-pyridinyl)pyrrolidinyl amine; N-[(3R)-1-(6-chloro-5-methyl-3-pyridinyl)pyrrolidinyl]-N-methylamine; (3S)-1-(6-chloro-5-methyl-3-pyridinyl)pyrrolidinylamine; N-[(3S)-1-(6-chloro-5-methyl-3-pyridinyl)pyrrolidinyl]-N-methylamine; (3S)-1-(5,6-dichloro-3-pyridinyl)pyrrolidinylamine; N-[(3S)-1-(5,6-dichloro-3-pyridinyl)pyrrolidinyl]-N-methylamine; (3R)-1-(5,6-dichloro-3-pyridinyl)pyrrolidinylamine; N-[(3R)-1-(5,6-dichloro-3-pyridinyl)pyrrolidinyl]-N-methylamine; (3S)-1-(6-chloro-5-methoxy-3-pyridinyl)pyrrolidinylamine; N-[(3S)-1-(6-chloro-5-methoxy-3-pyridinyl)pyrrolidinyl]-N-methylamine; (3S)-1-(6-fluoro-5-methyl-3-pyridinyl)pyrrolidinylamine; N-[(3S)-1-(6-fluoro-5-methyl-3-pyridinyl)pyrrolidinyl]-N-methylamine; N-[(3S)-1-(6-fluoro-5-methyl-3-pyridinyl)pyrrolidinyl]-N-methylamine; (3R)-1-(6-fluoro-5-methyl-3-pyridinyl)pyrrolidinylamine; N-[(3R)-1-(6-fluoro-5-methyl-3-pyridinyl)pyrrolidinyl]-N-methylamine; (3S)-1-(5-nitro-3-pyridinyl)pyrrolidinylamine; N-methyl-N-[(3S)-1-(5-nitro-3-pyridinyl)pyrrolidinyl]amine; (3R)-1-(5-nitro-3-pyridinyl)pyrrolidinylamine; N-methyl-N-[(3R)-1-(5-nitro-3-pyridinyl)pyrrolidinyl]amine; and (2S,3R)-2-(chloromethyl) 1-(3-pyridinyl)pyrrolidinylamine. Compounds corresponding to formula (viii) are described in further detail in International Publication WO 00/71534; and U.S. Pat. No. 6,833,370 (each of which is hereby incorporated by reference herein in its entirety).

In another particular embodiment, the compound is an indazole, benzothioazole, or benzoisothiazole. According to this embodiment, for example, the compound administered to the patient may have the formulae (ix)(a), (ix)(b), (ix)(c), or (ix)(d):

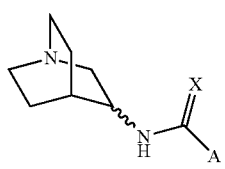
(ix)(a)

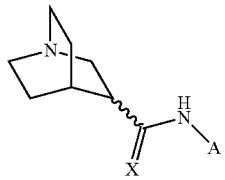
(ix)(b)

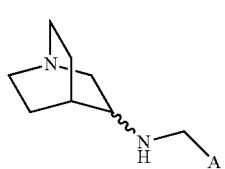
(ix)(c)

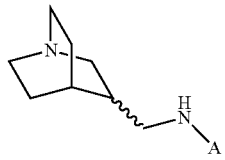
(ix)(d)

wherein A is:

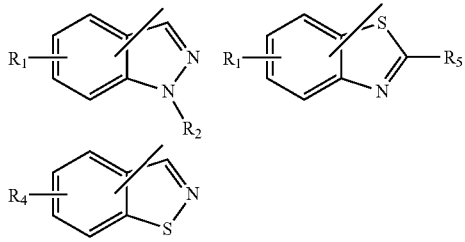

wherein the slanted line through the fused rings represent the bond of attachment from the fused chemical moiety to the remainder of the compound; X is O or S; $R_1$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het; $R_2$ is H, alkyl having 1 to 4 carbon atoms, cycloalkyl having 3 to 7 carbon atoms, or cycloalkylalkyl having 4 to 7 carbon atoms; $R_3$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het; $R_4$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., $OCH_3$), cycloalkoxy having 3 to 7 carbon atoms, cycloalkylalkoxy having 4 to 7 carbon atoms, alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het; $R_5$ is H, F, Cl, Br, I, OH, CN, nitro, $NH_2$, alkyl having 1 to 4 carbon atoms, fluorinated alkyl having 1 to 4 carbon atoms (e.g., $CF_3$), cycloalkyl having 3 to 7 carbon atoms, cycloalkylalkyl having 4 to 7 carbon atoms, alkoxy having 1 to 4 carbon atoms (e.g., OCH₃), cycloalkoxy having 3 to 7 carbon atoms, cycloalkylalkoxy having 4 to 7 carbon atoms, alkylthio having 1 to 4 carbon atoms (e.g., SCH₃), fluorinated alkoxy having 1 to 4 carbon atoms (e.g., OCF₃, OCHF₂), hydroxyalkyl having 1 to 4 carbon atoms, hydroxyalkoxy having 2 to 4 carbon atoms, monoalkylamino having 1 to 4 carbon atoms, dialkylamino wherein each alkyl group independently has 1 to 4 carbon atoms, Ar or Het; Ar is an aryl group containing 6 to 10 carbon atoms which is unsubstituted or substituted one or more times by alkyl having 1 to 8 carbon atoms, alkoxy having 1 to 8 carbon atoms, halogen (F, Cl, Br, or I, preferably F or Cl), dialkylamino wherein the alkyl portions each have 1 to 8 carbon atoms, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, alkylthio having 1 to 8 carbon atoms, alkylsulphinyl having 1 to 8 carbon atoms, alkylsulphonyl having 1 to 8 carbon atoms, monoalkylamino having 1 to 8 carbon atoms, cycloalkylamino wherein the cycloalkyl group has 3 to 7 carbon atoms and is optionally substituted, aryloxy wherein the aryl portion contains 6 to 10 carbon atoms (e.g., phenyl, naphthyl, biphenyl) and is optionally substituted, arylthio wherein the aryl portion contains 6 to 10 carbon atoms (e.g., phenyl, naphthyl, biphenyl) and is optionally substituted, cycloalkyloxy wherein the cycloalkyl group has 3 to 7 carbon atoms and is optionally substituted, sulfo, sulfonylamino, acylamido (e.g., acetamido), acyloxy (e.g., acetoxy) or combinations thereof; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) and is optionally substituted, alkyl having 1 to 8 carbon atoms, alkoxy having 1 to 8 carbon atoms, cyano, trifluoromethyl, nitro, oxo, amino, monoalkylamino having 1 to 8 carbon atoms, dialkylamino wherein each alkyl group has 1 to 8 carbon atoms, or combinations thereof; and pharmaceutically acceptable salts thereof.

Compounds corresponding to formulae (ix)(a), (ix)(b), (ix)(c), and (ix)(d) are described in further detail in U.S. Pat. No. 7,429,664 (which is hereby incorporated by reference herein in its entirety)

In general, for the compounds of formulae (i), (ii), (iii), (iv), (v), (vi), (vii), (viii), and (ix)(a-d), definitions for the chemical moieties recited in the various substituent groups are the same as those found in the patent or published application cited above in connection with the formulae. Also, with regard to stereoisomers, it should be understood that a solid line designation for the bonds in the compositions corresponding to formulae (i), (ii), (iii), (iv), (v), (vi), (vii), (viii), and (ix)(a-d) (and any others herein) for attachment of an substituent group to a chiral carbon atom of the compound indicates that these groups may lie either below or above the plane of the page (i.e., R or R ). All isomeric forms of the compounds disclosed herein are contemplated, including racemates, racemic mixtures, and individual enantiomers or diastereomers.

Another compound that may be used in the methods described herein is anabaseine, i.e., 2-(3-pyridyl)-3,4,5,6-tetrahydropyridine which is a naturally occurring toxin in certain marine worms (nemertine worms) and ants (see, e.g., Kem et al., Toxicon, 9:23, 1971) and is a potent activator of mammalian nicotinic receptors (see, e.g., Kem, Amer. Zoologist, 25, 99, 1985). Certain anabaseine analogs may also be employed, such as DMAB (3-[4-(dimethylamino) benzylidene]-3,4,5,6-tetrahydro-2',3'-bipyridin-e) (see, e.g., U.S. Pat. No. 5,602,257 and WO 92/15306 (each of which is hereby incorporated by reference herein), and (E-3-[2,4-dimethoxy-benzylidene]-anabasine, also known as GTS-21 and DMXB (see, e.g., U.S. Pat. No. 5,741,802 and U.S. Pat. No. 5,977,144 (each of which is hereby incorporated by reference herein in its entirety). Another compound that may be used tropisetron, i.e., 1αH, 5αH-tropan-3α-yl indole-3-carboxylate (see J. E. Macor et al., Bioorg. Med. Chem. Lett. 2001, 319-321).

Still other compounds having nicotinic acetylcholine receptor activity that may be used in the methods of the present disclosure include, for instance, U.S. Published Patent Application No. 2002/00288809; U.S. Published Patent Application No. 2009/0012127; U.S. Pat. No. 6,303,638; U.S. Pat. No. 6,846,817; U.S. Pat. No. 7,244,745; and U.S. Pat. No. 7,429,664 (each of which is hereby incorporated by reference herein).

Improving Ataxia and Non-Ataxic Imbalance

Also provided are methods for improving a symptom selected from ataxia and non-ataxic imbalance, or combinations thereof, in a patient. In general, the methods comprise administering to a patient exhibiting the symptom(s) a compound having nicotinic acetylcholine receptor activity, such as those described above. In one embodiment, the compound is selected from the group consisting of ABT-089, ABT-894, alpha-bungarotoxin, anabaseine, bupropion, buspirone, BW284c51, cytisine, dihydro-beta-erythoidine, DMXB, DMXB-A (GTS-21), diazoxon, donepezil, exelon, fluoxetine, galantamine, huperzine A, ispronicline (TC-1734/AZD-3480), lobeline, mecamylamine, MEM3454, MEM63908, methyllycaconitine, nefazodone, octanol/ethanol, OmIA, paroxetine, sertraline, tacrine, TC-2559, TC-5214 ((S)-(+)-mecamylamine), TC-5619, tebanicline (ABT-594), varenicline, venlafaxine, XY4083, and combinations thereof. In one another embodiment, the compound is selected from the group consisting of ABT-089, ABT-894, bupropion, cytisine, dianicline (SSR591813), DMXB-A (GTS-21), ispronicline (TC-1734/AZD-3480), lobeline, mecamylamine, methyllycaconitine, TC-2559, TC-5214 ((S)-(+)-mecamylamine), tebanicline (ABT-594), varenicline, and combinations thereof. In another embodiment, the compound is selected from the group consisting of donepezil, exelon, fluoxetine, galantamine, huperzine A, MEM3454, MEM63908, tacrine, XY4083, and combinations thereof. In one preferred embodiment, the compound is varenicline.

Generally, the methods involve first diagnosing or assessing the level of the ataxic or other symptom in the patient to provide a baseline level or measurement of the symptom (e.g., by virtue of its severity or intensity). Thereafter, the patient is administered (i.e., is treated with) a compound having nicotinic acetylcholine receptor activity, typically in the form of a pharmaceutical composition comprising the compound and a pharmaceutically acceptable carrier.

At some point during or after administration of the compound (e.g., 5 minutes, 10 minutes, 15 minutes, 30 minutes, 1 hour, 3 hours, 6 hours, 12 hours, 18 hours, 24 hours, 36 hours, 48 hours, or 72 hours, or longer (e.g., weeks, months, etc.), the patient's symptoms are again diagnosed or assessed. That is, a second measurement or level of the symptoms is taken; this measurement may be designated as a midpoint level or an endpoint level, depending on whether or not more treatments (i.e., further administrations of the compound) and/or symptom assessments are contemplated. The second (or subsequent) measurement may be compared to the baseline measurement to evaluate the efficacy of the treatment. Preferably, the second (or subsequent) measurement (as a midpoint or endpoint) taken after administration of the compound is improved relative to the baseline measurement.

This treatment and assessment regime may be repeated as many times as desired, with second, third, fourth, fifth, and so on, measurements being compared to the original baseline measurement taken prior to administration of the compound or otherwise initiating treatment. Assessments can be taken while the patient is still on a treatment regime (i.e., during the period of time that the patient is given the compound and while it is present in their system), and assessments may also be taken after a patient has stopped treatment and/or after complete washout or elimination of the compound from the patient's system.

Various scales can assess symptoms of ataxia and non-ataxic imbalance in a patient and the effect of the compounds described herein on the treatment of the symptom. These are, for example, and without limitation, the Scale for the Assessment and Rating of Ataxia (SARA), Friedreich's Ataxia Rating Scale (FARS), International Cooperative Ataxia Rating Scale (ICARS), Pourcher and Barbeau Ataxia Clinical Rating Scale, the Unified Multiple System Atrophy Rating Scale (UMSARS), and the like. The SARA, for example, is described by Schmitz-Hubsch et al., Neurology 66, 1717-1720 (2006). The FARS, for example, is described in Lynch et al., Neurology 2006; 66:1711-1716. The ICARS, for example, is described in Trouillas et al., J. Neurological Sciences 1997; 145(2):205-211. The Pourcher and Barbeau scale is described, for example, in Leone et al., Ital. J. of Neurological Sciences 1986; 7(1):61-62. Some of these and other ratings scales are described in Herndon, Handbook of Neurologic Rating Scales (2nd ed. 2006).

These scales or measures generally are carried out by observing the patient (e.g., watching the patient perform or attempt to perform certain tasks) and assigning a score based on the intensity or frequency of the symptoms and the ability, partial ability, or inability of the patient to perform various tasks. The scales may also target or focus upon improvements in symptoms since a previous assessment. In certain embodiments, a total or overall score on the assessment or scale is calculated. If desired, multiple scales or tests can be administered and their results combined. Typically, a baseline score is compared to a second, subsequent (midpoint or endpoint) score to determine the change in severity or frequency of ataxia or non-ataxic imbalance after treatment with the compound(s) described herein.

Once the compound has been administered, a patient's symptoms may remain improved relative to the baseline level, even after treatment has ceased and no further administrations of the compound a performed. The patient's symptoms may remain at an improved level, for example, for 1 day, 3 days, 5 days, 7 days, 3 weeks, 1 month, 3 months, 6 months, 1 year, or longer, after the final administration of the compound. In this regard, the methods described herein can be said to beneficially alter the chemical and/or biochemical pathways of the patient.

Administration and Mode of Treatment

In general, where the pharmaceutical agents discussed above are administered to a patient in need of treatment of one or more of the symptoms noted above, the agent is administered in an effective amount; that is, an amount to achieve a therapeutic benefit.

In general, the compound having nicotinic acetylcholine receptor activity is administered to the patient in the form of a pharmaceutical composition or pharmaceutical formulation comprising the compound. The compositions or formulations generally comprise at least one active pharmaceutical ingredient having nicotinic acetylcholine receptor activity and a pharmaceutically acceptable carrier (discussed in further detail below). The structure and synthesis of many nicotinic acetylcholine receptor-active compounds are well known to persons of skill in the art. A description of several representative compounds is provided above, and may also be found in the patent and other literature. This includes, for example, the patents and published applications cited herein, each of which is hereby incorporated by reference herein in its entirety.

The dose or amount of the pharmaceutical agent administered to the patient should be an effective amount for the intended purpose; i.e., treatment of one or more of the symptoms discussed above. Generally speaking, the effective amount of the agent administered to the patient can vary according to a variety of factors such as, for example, the age, weight, sex, diet, route of administration, and the medical condition of the patient. Specifically preferred doses are discussed more fully below, or are provided on the label of the pharmaceutical agent(s) being administered, or is within the ambit of one skilled in the art. It will be understood that the total daily usage of the compounds discussed herein will be decided by the attending physician within the scope of sound medical judgment.

The specific therapeutically effective dose level for any particular patient will depend upon a variety of factors including the disease, pathological disorder, or medical condition of the patient, and the particular symptoms being treated and the severity of the same; activity of the specific composition(s) employed; the age, body weight, general health, sex and diet of the patient; the time of administration; the route of administration; the rate of excretion of the specific composition(s) employed; the duration of the treatment; drugs used in combination or coincidental with the specific composition(s) employed and like factors are well known in the medical arts. For example, it is well within the skill of the art to start doses of the compositions(s) at levels lower than those required to achieve the desired effect, and to gradually increase the dosage until the desired effect is achieved. By way of another example, the dose level can be gradually or abruptly decreased to minimize undesired side effects of the compound being administered. If desired, the effective daily doses may be divided into multiple doses for purposes of administration. Consequently, single dose compositions may contain such amounts or submultiples to make up the daily dose.

Administration of the pharmaceutical agent can occur as a single event or over a time course of treatment. For example, one or more of the compositions can be administered hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compositions can be administered hourly, daily, weekly, bi-weekly, or monthly, for a period of several weeks, months, years, or over the lifetime of the patient. The pharmaceutical compositions may be administered to a patient on an empty stomach, or administered along with (i.e., before, during, or after) meals.

Dosage levels for the active agents are generally those indicated on the label of the pharmaceutical. One or more of the compounds may be utilized in a pharmaceutically acceptable carrier, additive or excipient at a suitable dose level ranging, for example, from about 0.05 to about 200 mg/kg of body weight per day, preferably within the range of about 0.1 to 100 mg/kg/day, most preferably in the range of 0.25 to 50 mg/kg/day. As noted above, the desired dose may conveniently be presented in a single dose or as divided doses administered at appropriate intervals, for example as two, three, four or more sub-doses per day.

Ideally, the active ingredient should be administered to achieve effective peak plasma concentrations of the active compound within the range of from about 0.05 uM to about 5 uM. Oral dosages, where applicable, will depend on the bioavailability of the compositions from the GI tract, as well as the pharmacokinetics of the compositions to be administered. For intravenous use, these concentrations may be achieved, for example, by the intravenous injection of about a 0.05 to 10% solution of the active ingredient, optionally in saline, or orally administered as a bolus containing about 1 mg to about 5 g, preferably about 5 mg to about 500 mg of the active ingredient, depending upon the active compound and its intended target. Desirable blood levels may be maintained by a continuous infusion to preferably provide about 0.01 mg/kg/hour to about 2.0 mg/kg/hour or by intermittent infusions containing about 0.05 mg/kg to about 15 mg/kg of the active ingredient. Likewise, continuous (e.g., hourly or daily) oral administration may be desired or necessary. While it is possible that, for use in therapy, one or more compositions of the invention may be administered as the raw chemical, it is preferable to present the active ingredient as a pharmaceutical formulation, presented in combination with a pharmaceutically acceptable carrier, excipient, or additive.

As noted above, the above-described compounds are generally dispersed in a pharmaceutically acceptable carrier prior to administration to the patient. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a patient, especially a human.

The selection of a pharmaceutically acceptable carrier will also, in part, be a function of the route of administration. In general, the compositions can be formulated for any route of administration so long as the blood circulation system is available via that route. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. Typically, the route of administration is oral.

Pharmaceutically acceptable carriers for use in combination with the compounds described herein are well known to those of ordinary skill in the art and are selected based upon a number of factors: the particular compound used, and its concentration, stability and intended bioavailability; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in formulations are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the active agents described above may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. Typically, the active agent is administered in tablet or pill form, including, for example, soft chewable tablets, hard chewable tablets, and hard swallowable tablets; various sizes and shapes of tablets may be formed, generally by varying the size and shape of the die and punch. Representative tablet shapes include briquette, circular (i.e., cylindrical), lozenge, and pillow shapes. The size and shape of the tablet may depend, in part, on the various components in the tablet and their amounts relative to other components in the tablet.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

OBJECTIVE: To assess the preliminary efficacy of varenicline (Chantix®) in treating cerebellar symptoms of spinocerebellar ataxia (SCA) and Fragile-X-Associated Tremor Ataxia Syndrome (FXTAS).

BACKGROUND: Varenicline, a partial agonist at nicotinic 42 receptors, may improve cerebellar symptoms in SCA (Example 2) and in FXTAS (Example 1).

DESIGN/METHODS: Seven patients from an academic movement disorders center with spinocerebellar ataxia (n=6) and FXTAS (n=1), were treated with open-label varenicline 1 mg twice daily. Two patients had genetically confirmed SCA 3, 1 patient had genetically confirmed SCA 6, 3 patients had sporadic cerebellar ataxia with no family history, and 1 patient had genetically-confirmed FXTAS. Patients were treated for 4 weeks with varenicline, which was discontinued on day 30. They were assessed at baseline and after 4 weeks using the Scale for the Assessment and Rating of Ataxia (SARA) (Schmitz-Hubsch et al, 2006) and the Clinical Global Impression (CGI) scale. Ataxia experts blindly assessed videotapes of the patients. RESULTS: Two patients (one with SCA 6 and one with sporadic ataxia) discontinued varenicline due to flu-like symptoms and increased tremor. In the remaining 5 patients, there was a mean improvement of 2.4 points in gait scores and of 5 points for the total SARA scores with varenicline use. Three patients had marked improvement, and 2 had moderate improvement in gait with varenicline use as measured by the CGI. Two of the patients who had marked improvement in gait with varenicline were smokers, and reduced their intake of cigarettes by 50% while taking varenicline.

CONCLUSIONS/RELEVANCE: Varenicline was shown to effectively treat cerebellar symptoms in this blinded video analysis of ataxic patients. Further controlled studies are warranted to investigate the effect of varenicline and smoking on cerebellar symptoms.

Example 1

The Fragile X-associated Tremor Ataxia syndrome (FXTAS) is a neurodegenerative disorder that occurs in adult males over the age 50 who are carriers of the fragile x mental retardation 1 (FMR-1) premutation. FXTAS symptoms include intention and postural tremor, ataxia, cognitive decline, parkinsonism, and autonomic dysfunction (1). Currently, there is no effective treatment for ataxia. We report the case of a man with FXTAS whose ataxia and imbalance were greatly improved after starting varenicline in an effort to stop smoking. Discontinuation of varenicline resulted in a worsening of the gait ataxia. Open-label resumption of varenicline has led to a sustained response of five months.

The patient was a 64-year old man with a nine-year history of postural and intention tremor of his arms and a four-year history of gait ataxia. His symptoms became disabling in the past year with frequent falls despite the intermittent use of a walker. His tremor along with progressive dysarthria and memory loss had significantly impaired activities of daily living for one year.

The patient was identified by a known pedigree in which the patient's granddaughter and grandson (born to his daughter) have Fragile X syndrome (>200 CGG repeats in the FMR1 gene). He was subsequently diagnosed with FXTAS, on the basis of the FMR1 premutation (90 CGG trinucleotide repeats) and published clinical criteria (1). His maternal aunt and his mother were premutation carriers, and two of his four brothers had postural and intention tremor and gait ataxia. His past medical history revealed he was treated for depression 35 years ago but was otherwise non-contributory. He denied current depression. He smoked up to two packs of cigarettes per day for 50 years, drank one to two alcoholic beverages per week but was never intoxicated. He was taking no medications.

A timeline of the patient's clinical course is depicted in FIG. 1. The patient started varenicline one mg twice daily which helped him quit smoking in a few days. One week after taking varenicline, he noted that his walking improved and he no longer needed assistance from a walker to ambulate. There was also marked improvement in his balance. The only side effect from varenicline was vivid dreaming, which occurred two days after starting it.

The patient was evaluated by the University of South Florida (USF) movement disorders center seven weeks after starting varenicline. Vital signs and physical examination were normal. His neurological examination included a Mini Mental State Exam (MMSE) of 26/30, mild dysarthria, mild voice tremor, severe postural and intention tremor of his arms, mild rigidity, and moderate dysmetria in all extremities. He was able to get out of a chair without assistance, and continued to walk six meters five times (30 meters total) without rest or the assistance of a walker. He was able to tandem walk for two to three steps. The rest of his neurological exam, including cranial nerves, reflexes, motor and sensory examination, was within normal limits. The patient received a score of 5 (out of a maximum possible score=63) on a Beck's Depression Scale (BDI) (2). A magnetic resonance image (MRI) of the brain showed hyperintensities of the middle cerebellar peduncles typical of FXTAS along with cortical and cerebellar volume loss (FIG. 2). Chest X-ray was clear, with no evidence of neoplasia.

The patient stopped varenicline seven weeks after starting it. Within 10 days, he reported a slight worsening of the residual ataxia and imbalance. Within three weeks, he again needed a walker for ambulation and began to fall daily. The patient returned to clinic off varenicline. His vital signs and physical examination were normal, and his neurological examination returned to the pre-varenicline state. He once again needed assistance to walk and was unable to tandem walk even with assistance. The rest of the neurological examination remained unchanged, including the postural and intention tremor. The BDI score had not changed.

At week 11, the patient re-started varenicline one mg twice daily, and again noted improvement in ataxia within one week. Due to vivid dreams, the varenicline dose was decreased to one mg daily at week 12. The patient has taken varenicline for 22 weeks, with a sustained ataxia improvement.

A videotape of the patient was scored by a blinded movement disorders expert using the SARA (Scale for Assessment and Rating of Ataxia) (3). The SARA scores on varenicline one mg b.i.d. were "two" for functional staging for ataxia (ataxic symptoms were present and were recognized by patient, but were still mild), "one" for tandem walking (the patient was able to tandem walk in less than perfect manner or the patient could tandem walk greater than four sequential steps but less than eight steps) and "zero" for gait (normal). The SARA scores after the patient had discontinued varenicline for three weeks included a "three" for functional staging for ataxia (ataxic symptoms considered overt and significant), "three" for tandem walking (the patient was considered too poorly coordinated to attempt the task), and "two" for gait (the patient walked with definite ataxia; may have needed intermittent support for walking or the examiner needed to walk with patient for safety sake).

Varenicline is a highly selective partial agonist at the $\alpha 4\beta 2$ nicotinic acetylcholine receptor that is approved by the FDA for smoking cessation. In this case report, a patient with FXTAS experienced marked improvement in gait ataxia and imbalance while taking varenicline. The clinical observations in this case are supported by a blinded rating of videotapes taken during and after varenicline use, and a re-emergence of ataxia and imbalance shortly after varenicline was discontinued.

Effective treatment of ataxia and imbalance is currently lacking. Case series and small controlled trials of several medications including buspirone, fluoxetine, zolpidem, and lamotrigine have demonstrated either conflicting results or limited efficacy (4).

As noted above, recent reports suggest that selective activation of the $\alpha 4\beta 2$ nicotinic acetylcholine receptor subtype may improve alcohol (10) and tetrahydrocannabinoid [$\Delta^9$THC]-induced ataxia in experimental animals (11). It is known that selective activation of $\alpha 4\beta 2$ nicotinic acetylcholine receptors results in post-synaptic up-regulation (i.e., desensitization) of dopamine receptors in the mesolimbic system (12,13). This may be relevant to tolerance and dependence, but it is unlikely to explain the anti-ataxic effect of varenicline. Early evidence suggests instead that other neurotransmitters like glutamate can modulate nicotine-mediated attenuation of ethanol-induced ataxia (10). In addition, increased nitric oxide (NO) production following intracerebellar injection of the $\alpha 4\beta 2$ nicotinic acetylcholine receptors agonist RJR-2403 may improve $\Delta^9$THC-induced ataxia via a mechanisms of cross tolerance mediated through the powerful NO intracellular signaling system (11). These and other non-dopaminergic actions of varenicline await further investigation.

Because the patient stopped smoking at the same time varenicline was started, it is plausible that smoking cessation led to gait improvement. However, this is unlikely, because there was a re-emergence of ataxia when varenicline was discontinued, although smoking had been discontinued several weeks before. The patient drank alcohol occasionally, and the possibility that varenicline might have reduced alcohol-induced ataxia, rather than that solely caused by FXTAS, must also be entertained.

Further controlled studies on the effect of varenicline to improve ataxia and imbalance are warranted. Caution is needed, as varenicline is associated with potential risks of suicidal behavior, depressed mood, and agitation.

1. Jacquemont S, Hagerman R J, Leehey M, et al. Fragile X premutation tremor/ataxia syndrome: molecular, clinical, and neuroimaging correlates. *Am J Hum Genet.* 2003; 72(4):869-78.
2. Beck A. T., Ward C., Mendelson M. (1961). "Beck Depression Inventory (BDI)". Arch Gen Psychiatry 4: 561-571.
3. Schmitz-Hübsch T, du Montcel S T, Baliko L, et al. Scale for the assessment and rating of ataxia: development of a new clinical scale. Neurology. 2006 Jun. 13; 66(11):1717-20.
4. Assadi M, Campellone J V, Janson C G, Veloski J J, Schwartzman R J, Leone P. Treatment of spinocerebellar ataxia with buspirone. J Neurol Sci. 2007 Sep. 15; 260 (1-2):143-6.
5. Falk L, Nordberg A, Seiger A, Kjaeldgaard A, Hellstreöm-Lindahl E. Smoking during early pregnancy affects the expression pattern of both nicotinic and muscarinic acetylcholine receptors in human first trimester brainstem and cerebellum. Neuroscience 2005; 132:389-397.
6. Chen W J, Edwards R B, Romero R D, Parnell S E, Monk R J. Long-term nicotine exposure reduces Purkinje cell number in the adult rat cerebellar vermis. Neurotoxicol Teratol. 2003 May-June; 25(3):329-34.
7. Chen W J A, Parnell S E, West J R. Nicotine decreases blood alcohol concentration in neonatal rats. Alcohol Clin Exp Res 2001; 25:1072-1077.
8. Pereira C B, Strupp M, Holzleitner T, Brandt T. Smoking and balance: correlation of nicotine-induced nystagmus and postural body sway. NeuroReport 2001; 8:1223-1226.
9. Spillane J D. The effect of nicotine on spinocerebellar ataxia. Br Med J 2: 1345, 1955. 1345-1351.
10. Al-Rejaie S, Dar M S. Behavioral interaction between nicotine and ethanol: possible modulation by mouse cerebellar glutamate. Alcohol Clin Exp Res. 2006 July; 30(7):1223-33.
11. Smith A D, Dar M S. Mouse cerebellar nicotinic-cholinergic receptor modulation of Delta9-THC ataxia: role of the alpha4beta2 subtype. Brain Res. 2006 Oct. 18; 1115(1):16-25.
12. Katz B, Thesleff A. A study of 'desensitization' produced by actylcholine at the motor end plate. J Physiol 1967; 138:63-80.
13. Arneric S P, Holladay M, Wiliams M. Neuronal nicotinic receptors: A perspective on two decades of drug discovery research. Biochemical Pharmacology 2007; 74:1092-1101.

Example 2

Spinocerebellar ataxia (SCA) is a group of inherited neurodegenerative disorders characterized by progressive gait dysfunction, imbalance, impaired limb coordination, and altered speech. There is currently no effective treatment for any of the SCA disorders. We report the cases of 2 SCA patients (types 3 and 14) who experienced marked improvement in their cerebellar symptoms, including ataxia and imbalance, while taking varenicline (Chantix®, Pfizer, New York, N.Y.), a drug approved to aid smoking cessation.

The first patient was a 63-year old woman with a 16-year history of imbalance, gait dysfunction, and dysarthria who presented to an academic movement disorders center for management of her symptoms. She had been diagnosed with SCA type 3 twelve years ago by genetic testing, and had a 3-generation history of SCA type 3. Her medical history included one myocardial infarction 2 years ago, coronary artery disease, hypertension, and hyperlipidemia. The patient had a 50-pack year history of smoking cigarettes.

On examination, the patient's vital signs and physical examination were normal. Her neurologic examination included a Mini-Mental Status Exam (MMSE) of 30/30, mild dysarthria, mild to moderate postural and intention tremor, mild dystonia in her arms, mild akinesia, and moderate dysmetria in all extremities. Fast alternating hand movements were irregular and marked by interruptions, and her heel to shin slide was severely abnormal bilaterally. Her gait was ataxic and dysmetric, and she required the constant use of a walker or the support of a cane to ambulate. Her cranial nerves and motor examination were normal, although there was mild decrease in her sensory examination to light and deep touch in a stocking-glove distribution. There was increased tone and hyperreflexia in her lower extremities. A recent magnetic resonance image (MRI) of the brain showed marked atrophy of the cerebellum.

After the evaluation, the patient started varenicline 0.5 mg twice daily for smoking cessation. The dose of varenicline was increased to 1 mg twice daily after one week. Ten days after starting varenicline, the patient reported that she had an improvement in depth perception, and that her walking seemed easier and more stable. Twenty-one days after first taking varenicline, the patient was able to walk for 3 blocks using only a cane rather than a walker, with markedly improved balance. However, she did not stop smoking cigarettes at any time while taking varenicline.

The patient returned to the academic movement disorders center one month after starting varenicline for routine follow-up. Her gait dysfunction and akinesia improved markedly, and she was able to walk independently while only occasionally reaching for the wall for stability. Limb dysmetria, fast alternating movements, finger to nose and heel-shin slide also markedly improved. A videotape of the patient was scored by a blinded movement disorders expert using the SARA (Scale for Assessment and Rating of Ataxia) (1). The total SARA score prior to the patient taking varenicline 1 mg twice daily was 29, while the score one month after starting varenicline was 13.

The second patient was a 51-year old woman who presented to an academic movement disorders center for neurologic evaluation. After a 1-year history of imbalance, incoordination, and speech disturbance, she received genetic testing that revealed mutations in the PRKCG gene, corresponding to the SCA14 locus on chromosome 19q13.4-qter. The patient's brother and father demonstrated symptoms of incoordination and clumsiness that were attributed to prior motor vehicle accidents, although neither had received genetic testing for SCA. The patient was of German and Dutch ancestry. She had never smoked or used drugs or alcohol and had no allergies. Her medical history was significant for hypertension, which was treated with 325 mg of valsartan (Diovan). Prior medications to treat her cerebellar symptoms included levodopa/carbidopa (Sinemet), lorazepam (Ativan), clonazapem (Klonopin), and zolpidem (Ambien), to no avail.

On evaluation, the patient's vital signs and physical examination were normal. Her neurologic examination included a Mini-Mental Status Examination of 30/30, mild dysarthria, mild postural and intention tremor, and moderate dysmetria in all extremities. Her gait consisted of moderate to severe ataxia, and she required the constant use of a walker or the support of a cane to ambulate. The patient could tandem walk only with support. Increased tone and hyperreflexia were present in her lower extremities, with occasional myoclonus of her right leg. A recent magnetic resonance imaging of the brain showed cerebellar atrophy.

The patient was started on 0.5 mg of varenicline (Chantix®) once a day, titrating to 1 mg twice daily after 1 week with the understanding that this was being used as an off-label medication. She complained of nausea for 7 days after taking the medication, but reported marked improvements in walking, coordination, speech, and balance 8 days after starting varenicline. The patient returned to the academic movement disorders center 3 weeks after starting varenicline. Her gait dysfunction improved markedly so that she could walk without assistance. Other symptoms including speech, dysmetria, and finger-to-nose and heel-to-shin maneuvers also markedly improved. The patient was scored by a blinded movement disorders expert using the SARA. The patient's total SARA score before taking 1 mg of varenicline twice daily was 22, whereas the score 3 weeks after starting varenicline was 8. The patient remained on varenicline for 8 weeks with continued efficacy but discontinued it owing to financial considerations. She was reexamined 4 weeks after discontinuing varenicline, and her neurologic examination had returned to prevarenicline status.

Varenicline is a highly selective partial agonist at α4β2 nicotinic acetylcholine receptors and a full agonist at α7 nicotinic acetylcholine receptors (2). The exact mechanism of action for the beneficial effect of varenicline in these cases is unknown. It has been postulated that nicotinic acetylcholine receptor subunits are involved in the modulating cerebellar activity in humans (3). Nicotinic acetylcholine receptors α3, α4, α6, and α7 have been localized in Purkinje cell and granule cell layers in human autopsy specimens suggesting that these receptors are present in nerve terminals of the cerebellum (3). Further, selective activation of the α4β2 nicotinic acetylcholine receptor subtype improves alcohol (4) and tetrahydrocannabinoid [$\Delta^9$THC]-induced ataxia in animals (5).

There is no effective treatment of ataxia, and case series and small controlled trials of several medications including antianxiolytics, antidepressants, and antiepileptics have shown limited efficacy or have been conflicting (6). Thus, controlled studies on the effect of varenicline on ataxia and imbalance are warranted. Adverse effects of varenicline include nausea, sleep disturbance, constipation, flatulence, and vomiting. Caution is needed in prescribing varenicline owing to its recent reports of suicidal behavior associated with its use.

1. Schmitz-Hübsch T, du Montcel S T, Baliko L, et al., Scale for the assessment and rating of ataxia: development of a new clinical scale. Neurology. 2006 Jun. 13; 66(11):1717-20.
2. Mihalak K B, Carroll F I, Luetje C W, Varenicline is a partial agonist at alpha4beta2 and a full agonist at alpha7 neuronal nicotinic receptors. Mol. Pharmacol. 2006; 70(3):801-805.
3. Graham A, Court J A, Martin-Ruiz C M et al., Immunohistochemical localisation of nicotinic acetylcholine receptor subunits in human cerebellum. Neuroscience 2002; 113(3):493-507.
4. Al-Rejaie S, Dar M S, Behavioral interaction between nicotine and ethanol: possible modulation by mouse cerebellar glutamate. Alcohol Clin. Exp. Res. 2006; 30(7): 1223-1233.
5. Smith A D, Dar M S, Mouse cerebellar nicotinic-cholinergic receptor modulation of Delta9-THC ataxia: role of the alpha4beta2 subtype. Brain Res. 2006; 1115(1):16-25.
6. Chen W J, Edwards R B, Romero R D, et al., Long-term nicotine exposure reduces Purkinje cell number in the adult rat cerebellar vermis. Neurotoxicol Teratol 2003; 25(3):329-334.

What is claimed is:

1. A method of treating the loss or failure of muscular coordination resulting from type 3 or type 14 Spinocerebellar ataxia or fragile X/tremor ataxia syndrome in a human, the method comprising administering varenicline to the human.
2. The method of claim 1 wherein the method is for treating ataxia resulting from type 3 Spinocerebellar ataxia.
3. The method of claim 1 wherein the method is for treating ataxia resulting from type 14 Spinocerebellar ataxia.
4. The method of claim 1 wherein the method is for treating ataxia resulting from fragile X/tremor ataxia syndrome.

* * * * *

UNITED STATES PATENT AND TRADEMARK OFFICE
CERTIFICATE OF CORRECTION

PATENT NO. : 9,463,190 B2
APPLICATION NO. : 12/934913
DATED : October 11, 2016
INVENTOR(S) : Theresa A. Zesiewicz and Kelly L. Sullivan It is certified that error appears in the above-identified patent and that said Letters Patent is hereby corrected as shown below:

In the Specification

Column 14,
Lines 35-36, "-CN, -CF$_3$, -NO$_2$, -CH$_2$OH, -CH$_2$CN, alkoxy)" should read -- -CN, -CF$_3$, -NO$_2$, -CH$_2$OH, -CH$_2$CN, -(C$_1$-C$_3$ alkoxy)--.
Line 37, "-N(C$_3$-C$_3$ alkyl)" should read -- -N(C$_1$-C$_3$ alkyl)--.
Line 50, "-CONH(C$_3$-C$_3$ alkyl)" should read --CONH(C$_1$-C$_3$ alkyl)--.

Column 30,
Line 61, "Hellstreöm" should read --Hellström--.

Signed and Sealed this
Fourth Day of September, 2018

Andrei Iancu
*Director of the United States Patent and Trademark Office*